(12) United States Patent  (10) Patent No.: US 8,008,508 B2
Chen et al. (45) Date of Patent: Aug. 30, 2011

(54) ORGANOCATALYST

(75) Inventors: Kwunmin Chen, Taipei (TW);
Ying-Fang Ting, Taipei (TW);
Hsuan-Hao Kuan, Taipei (TW);
Pang-Min Liu, Taipei (TW); Chihliang Chang, Taipei (TW)

(73) Assignee: National Taiwan Normal University, Taipei (TW)

( * ) Notice: Subject to any disclaimer, the term of this patent is extended or adjusted under 35 U.S.C. 154(b) by 8 days.

(21) Appl. No.: 12/609,192

(22) Filed: Oct. 30, 2009

(65) Prior Publication Data

US 2011/0040104 A1  Feb. 17, 2011

(30) Foreign Application Priority Data

Aug. 14, 2009 (TW) .............................. 98127347 A

(51) Int. Cl.
*C07D 207/08* (2006.01)
(52) U.S. Cl. ...................................................... 548/570
(58) Field of Classification Search .................. 548/556, 548/541, 567, 566, 572, 571, 570
See application file for complete search history.

(56) References Cited

OTHER PUBLICATIONS

Chang et al. Adv. Synth. Catal. 2009, 351, 1273-1278.*
Canivet et al. Green Chem., 2007, 9, 391-397.*

* cited by examiner

*Primary Examiner* — Joseph Kosack
*Assistant Examiner* — Matthew Coughlin

(74) *Attorney, Agent, or Firm* — Peter F. Corless; Dwight D. Kim; Edwards Angell Palmer & Dodge LLP

(57) ABSTRACT

The present invention provides an organocatalyst of formula (I),

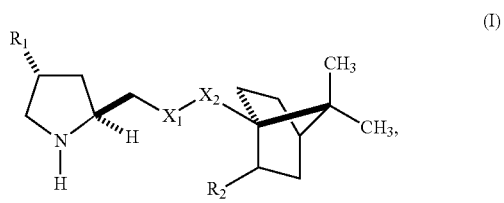

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; $R_2$ is —OH or =O; $X_1$ is one selected from the group consisting of —NH—, —S— and

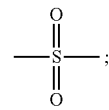

$X_2$ is one selected from the group consisting of —C(=O)—, —CH$_2$— and

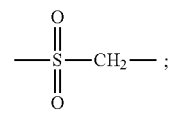

and $X_1$ is different from $X_2$. The high yield and enantioselectivity of an addition reaction are obtained by using the organocatalyst of the present invention.

5 Claims, 20 Drawing Sheets

ORGANOCATALYST

FILED OF INVENTION

The present invention relates to an organocatalyst, and more particularly, to an organocatalyst for enhancing yield and enantioselectivity.

BACKGROUND OF THE INVENTION

Asymmetric catalytic reactions are important in organic chemistry. In past thirty years, the asymmetric catalytic reaction is catalyzed by an organic chelating agent coupled to a metal center. However, the usage of metals results in environmental pollutions. Therefore, as the increased requirement of quality of pharmaceutical production, the catalyst using pure organic molecules other than the catalyst system having metals is a better and wiser choice in the industry.

In pharmaceutical chemistry, many organic intermediates depend on organocatalysts which are used for asymmetric catalytic reactions. Although some research has reported that asymmetric Michael addition reactions can be performed in water or saline solution, the solvents used in the reactions have influences in environment, and moreover, for certain compounds having no reaction in aqueous solution, the synthesis of pharmaceutical compound would be more difficult and complicated. In addition, the target yield is obtained by using even more than 50 mol % of the conventional organocatalysts.

Accordingly, it is an urgent issue to develop an organocatalyst with less amount for enhancing yield and enantioselectivity in a relatively mild condition, such as low toxicity, metals-free, aqueous solution or even solvent-free system.

SUMMARY OF THE INVENTION

The present invention provides an organocatalyst of formula (I),

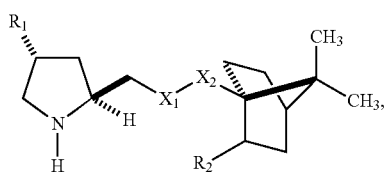

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; $R_2$ is —OH or =O; $X_1$ is one selected from the group consisting of —NH—, —S— and

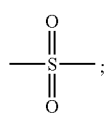

$X_2$ is one selected from the group consisting of —C(=O)—, —CH$_2$— and

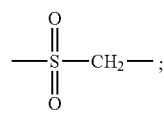

and $X_1$ is different from $X_2$.

In a preferred embodiment, the organocatalyst of the present invention has the following structure:

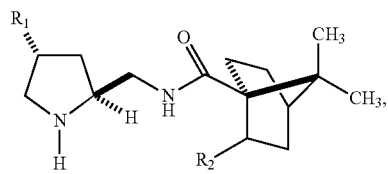

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; and $R_2$ is —OH or =O.

In one embodiment, the organocatalyst of the present invention has the following structure:

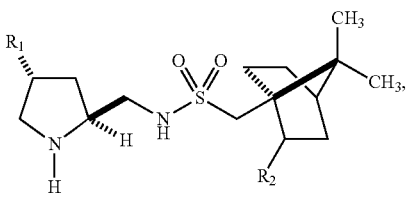

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; and $R_2$ is —OH or =O.

In one embodiment, the organocatalyst of the present invention has the following structure:

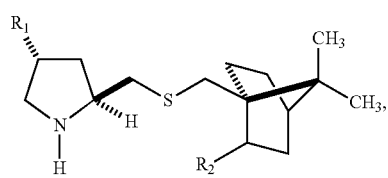

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; and $R_2$ is —OH or =O.

In one embodiment, the organocatalyst of the present invention has the following structure:

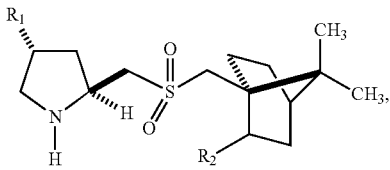

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; and $R_2$ is —OH or =O.

The present invention further provides a use of the organocatalyst for an addition reaction of a donor molecule and an acceptor molecule, wherein an amount of the organocatalyst is 5 to 25 mol % of an amount of the acceptor molecule. The organocatalyst of the present invention is preferably used an addition reaction such as Michael addition reaction. Also, the organocatalyst of the present invention increases yield and enantioselectivity in a solvent such as saline solution, and is more preferably used in Michael addition reaction in solvent-free condition.

In a preferred embodiment, the organocatalyst of the present invention is used in an addition reaction including an acid, which is 15 to 25 mol % of the amount of the acceptor molecule. The acid can be Bronsted acid. Specifically, the acid is p-toluenesulfonic acid, acetic acid, citric acid or benzoic acid. Preferably, the acid is citric acid or benzoic acid.

In a preferred embodiment, the organocatalyst of the present invention is used in an addition reaction, which is performed at a temperature ranging from −40 to 30° C. Generally, a temperature below −20° C. is unfavorable to Michael addition reaction, resulting in low yield with enantioselectivity. Thus, in Michael addition reaction, the preferred temperature is 0 to 30° C.

In one embodiment of Michael addition reaction, the reaction is performed for 12 to 60 hours, and preferably for 12 to 48 hours. Further, in the embodiment with addition of acid, the reaction is performed for 10 to 30 hours to have high yield and enantioselectivity. For example, when p-toluenesulfonic acid is used in the reaction at a temperature ranging from −5 to 30° C. for 10 to 24 hours, the yield is 77-80% and enantioselectivity is 79-85%.

In one embodiment of asymmetric α-amination reaction, the donor molecule is α-mono-substituted aldehyde, the acceptor molecule is an azo compound, and the reaction is performed at a temperature ranging from −40 to −20° C.

The organocatalyst of the present invention effectively catalyzes an addition reaction. Moreover, the organocatalyst of the present invention can increase yield and enantioselectivity in water-free or solvent-free condition.

DETAILED DESCRIPTION OF THE PREFERRED EMBODIMENTS

The detailed description of the present invention is illustrated by the following specific examples. Persons skilled in the art can conceive the other advantages and effects of the present invention based on the disclosure contained in the specification of the present invention.

The present invention provides an organocatalyst of formula (I),

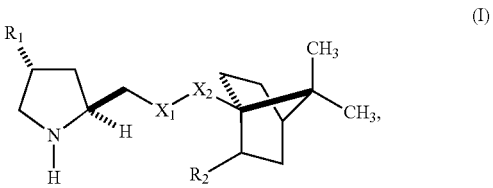

(I)

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl, phenyl and phenyl substituted with $C_{1-6}$alkyl; $R_2$ is —OH or =O; $X_1$ is one selected from the group consisting of —NH—, —S— and

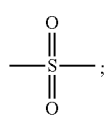

$X_2$ is one selected from the group consisting of —C(=O)—, —CH$_2$— and

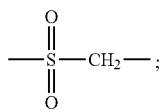

and $X_1$ is different from $X_2$.

Embodiment 1

Synthesis of a Representative Compound 3a of the Present Invention

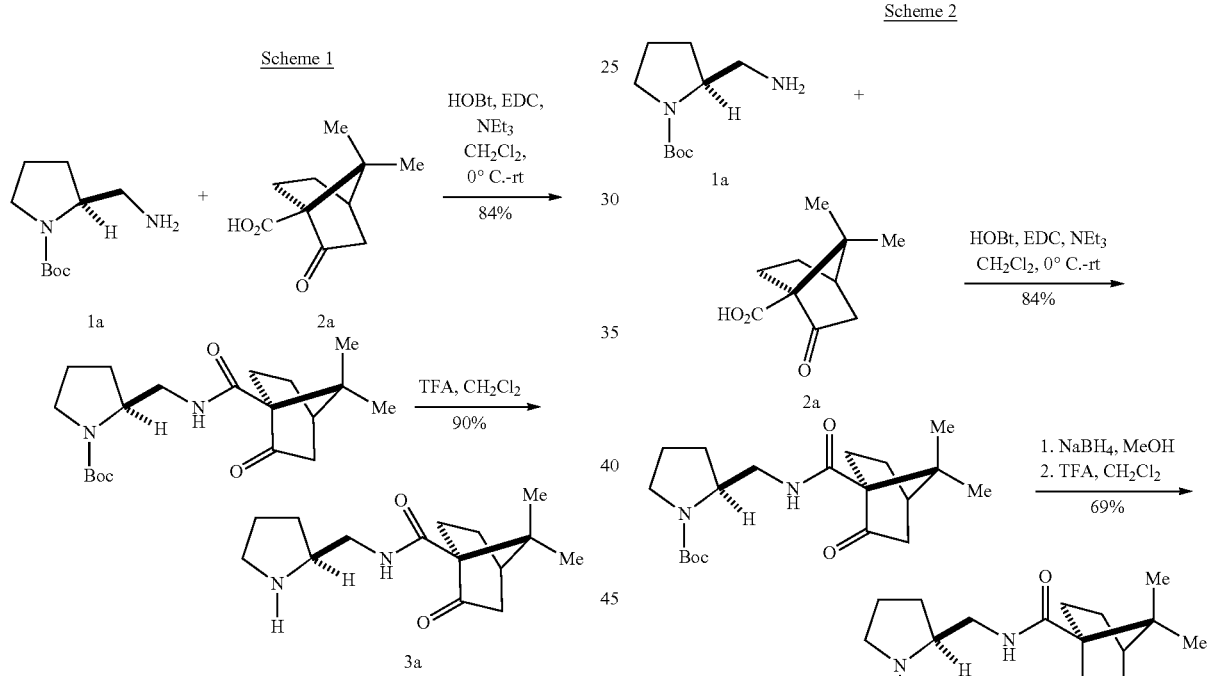

Scheme 1

N-Boc-(S)-2-aminomethylpyrrolidine (compound 1a, 3.0 g, 15 mmol) and (S)-ketopinic acid (compound 2a, 2.7 g, 15 mmol) were dissolved in 30 ml of dry dichloroethane, and then the mixture was added with triethylamine (2.27 ml, 15.75 mmol), hydroxybenzotriazole (HOBt) (2.27 g, 16.5 mmol) and 1-ethyl-3-dimethyl aminopropylcarbodiimide (EDC) (3.15 g, 16.5 mmol) at 0° C. The reaction was performed with stirring at room temperature for 4 hours, and then the solvent was removed. The residue was dissolved in 30 ml of dichloroethane. The mixture was washed with ammonium chloride solution and sodium bicarbonate solution, and then washed with saline solution and dried by magnesium sulfate. The mixture was filtered and concentrated under reduced pressure, and purified by column chromatography to obtain the amide compound.

Figure 1A:
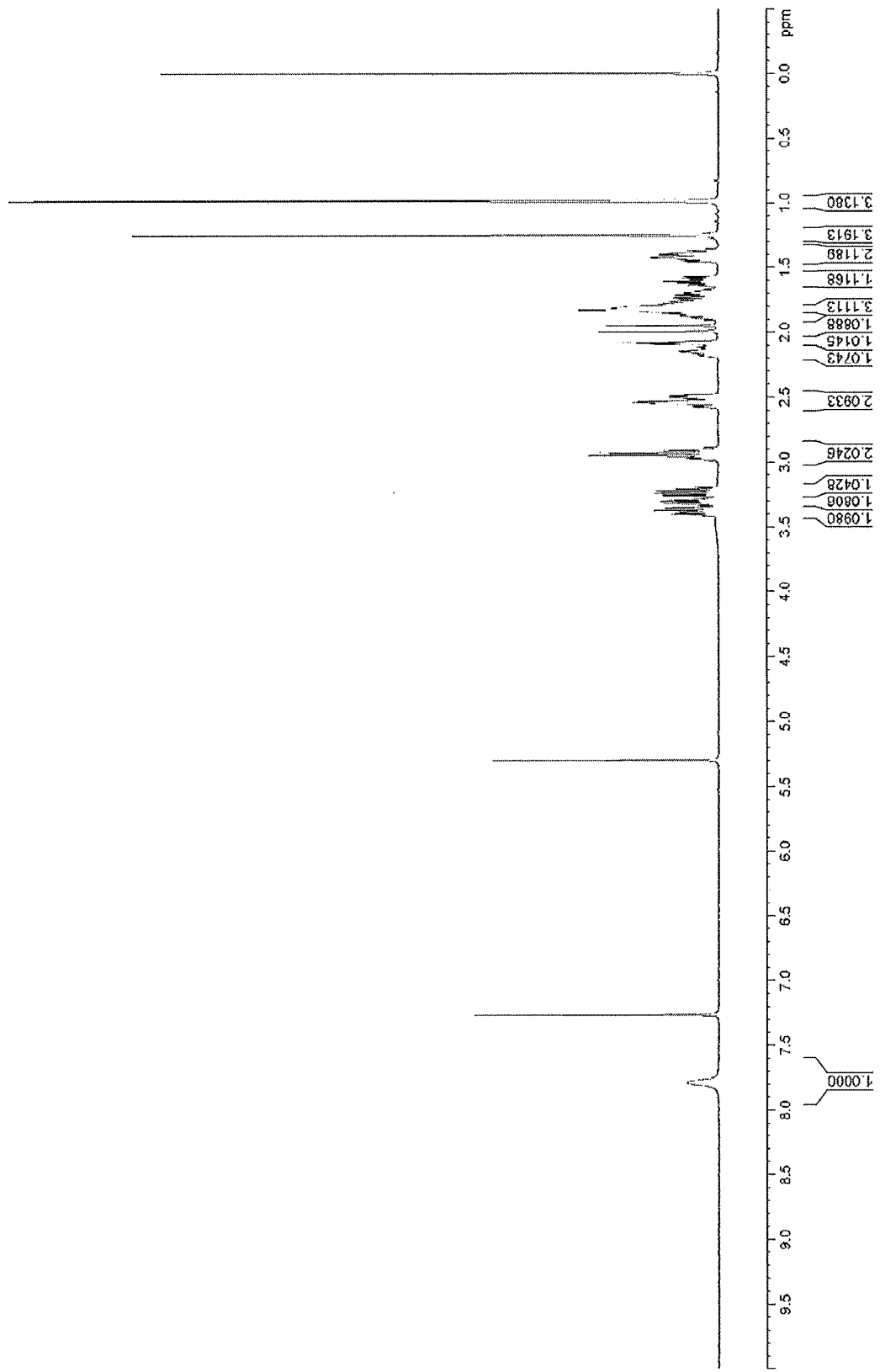
FIG. 1A shows $^1$H NMR of the organocatalyst 3a according to the present invention.
Figure 1B:
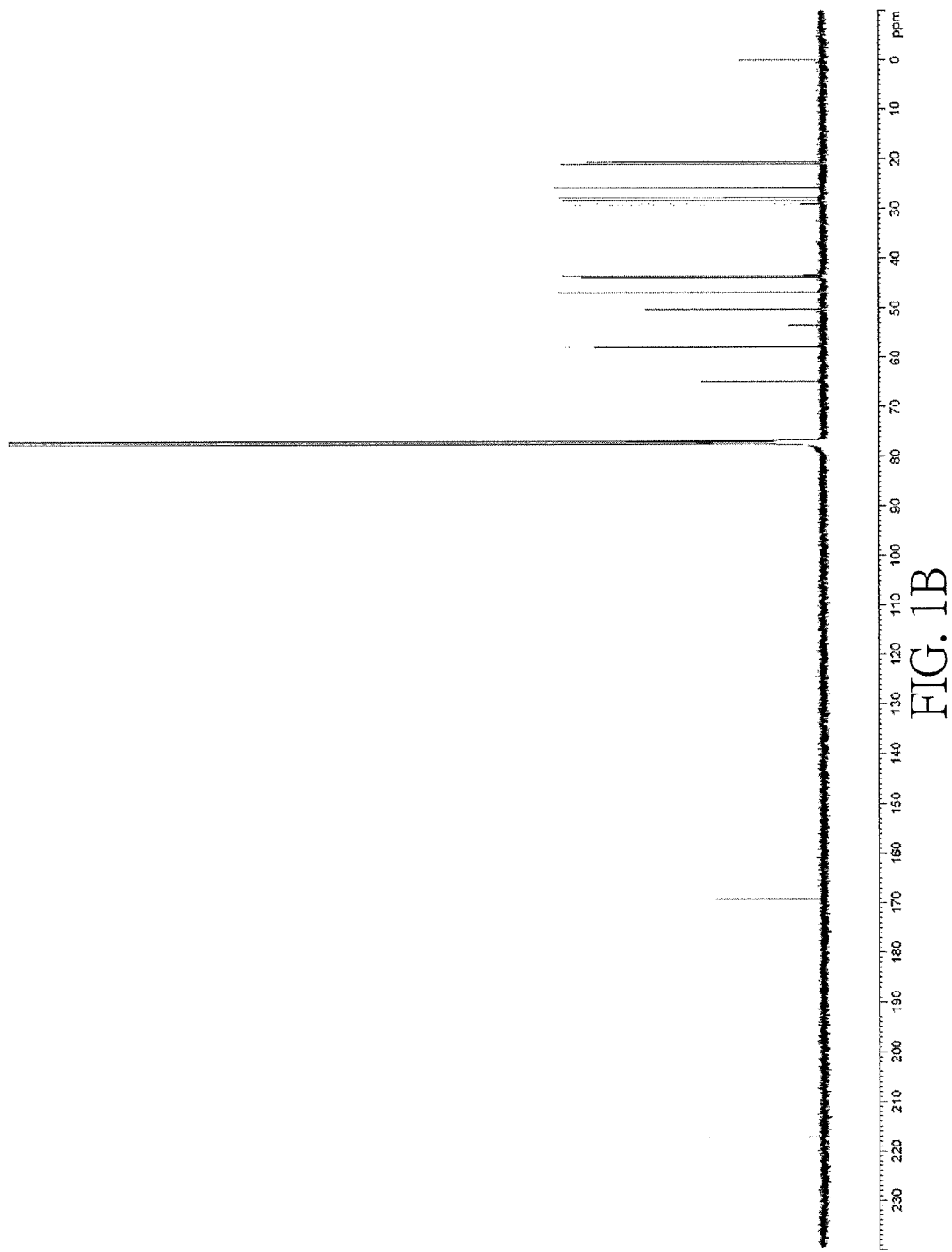
FIG. 1B shows $^{13}$C NMR of the organocatalyst 3a according to the present invention.

The amide compound was dissolved in 10 ml of dichloroethane, and then 1 ml of trifluoroacetic acid (TFA) was dropped into the mixture at room temperature. The mixture was stirred for 2 hours, and then diluted with dichloroethane and washed by 2N NaOH. The mixture was then washed by saline solution, dried by magnesium sulfate, filtered, concentrated under reduced pressure, and purified by column chromatography to obtain the organocatalyst 3a. Upon determination, $^1$H NMR and $^{13}$C NMR of the compound 3a were shown in FIG. 1A and FIG. 1B, respectively. $^1$H NMR (CDCl$_3$, 400 MHz)δ7.788 (s, 1H, NH), 3.43-3.35 (m, 1H), 3.35-3.27 (m, 1H, NH), 3.27-3.18 (m, 1H), 3.0-2.87 (m, 2H), 2.6-2.47 (m, 2H), 2.2-2.1 (m, 1H), 2.08(t, J=0.32 Hz, 1H), 1.97 (d, J=18.68 Hz), 1.85-1.77 (m, 3H), 1.65-1.56 (m, 1H), 1.47-1.35 (m, 2H), 1.25 (s, 3H), 0.99 (s, 3H); $^{13}$C NMR (CDCl$_3$, 400 MHz)δ217.19, 169.34, 64.89, 57.72, 50.11, 46.66, 43.84, 43.77, 43.33, 29.15, 28.30, 27.73, 25.73, 20.96, 20.52. HRMS (FAB$^+$) m/z (MH$^+$)=265.1919 (C$_{15}$H$_{25}$N$_2$O$_2$ calculated as 265.1916)

Embodiment 2

Synthesis of a Representative Compound 3b of the Present Invention

N-Boc-(S)-2-aminomethylpyrrolidine (compound 1a, 3.0 g, 15 mmol) and (S)-ketopinic acid (compound 2a, 2.7 g, 15 mmol) were dissolved in 30 ml of dry dichloroethane, and then the mixture was added with triethylamine (2.27 ml, 15.75 mmol), hydroxybenzotriazole (HOBt) (2.27 g, 16.5 mmol) and 1-ethyl-3-dimethyl aminopropylcarbodiimide (EDC) (3.15 g, 16.5 mmol) at 0° C. The reaction was performed with stirring at room temperature for 4 hours, and then the solvent was removed. The residue was dissolved in 30 ml of dichloroethane. The mixture was washed with ammonium chloride solution and sodium bicarbonate solution, and then washed with saline solution and dried by magnesium sulfate. The mixture was filtered and concentrated under reduced pressure, and purified by column chromatography to obtain the amide compound.

Figure 2A:
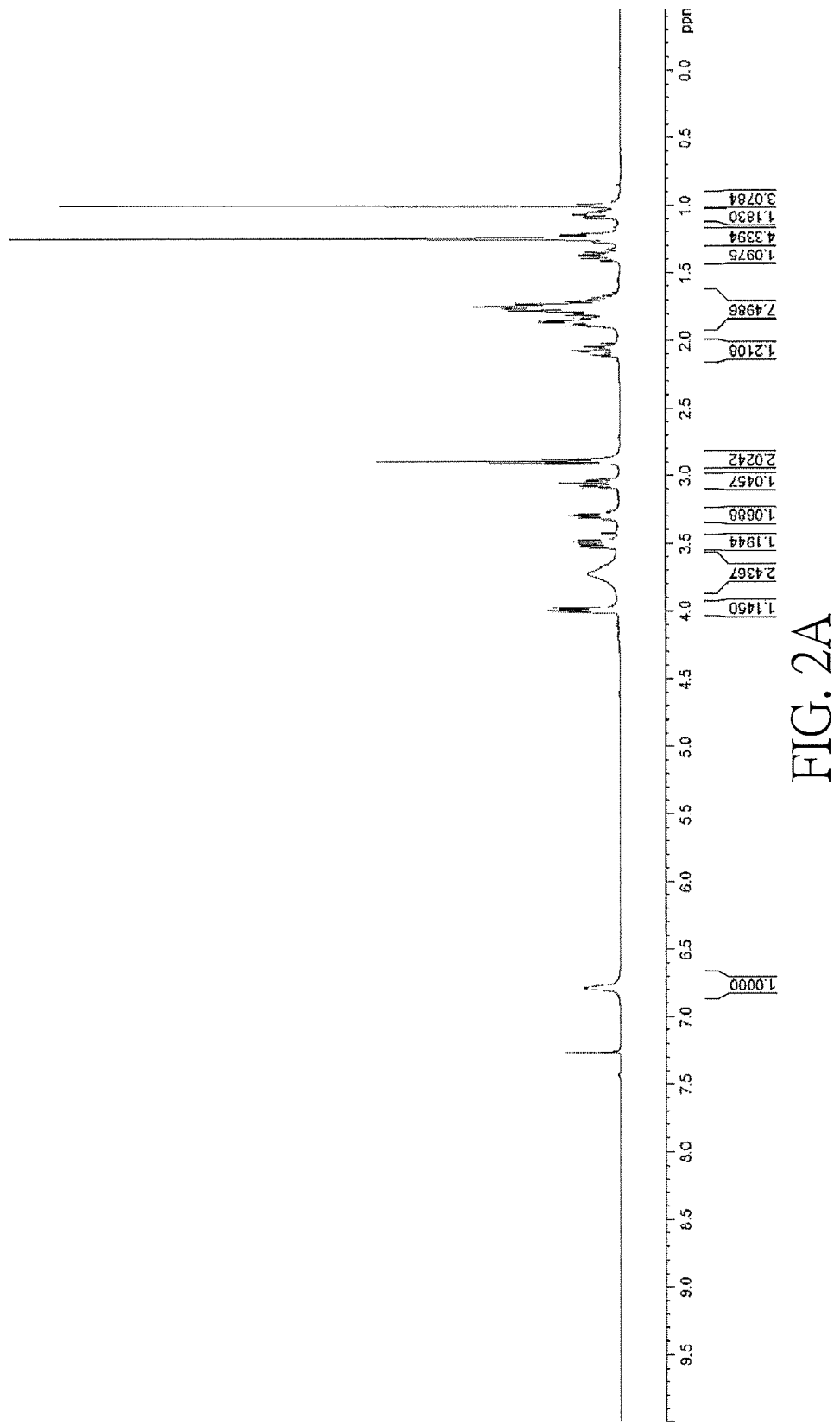
FIG. 2A shows $^1$H NMR of the organocatalyst 3b according to the present invention.
Figure 2B:
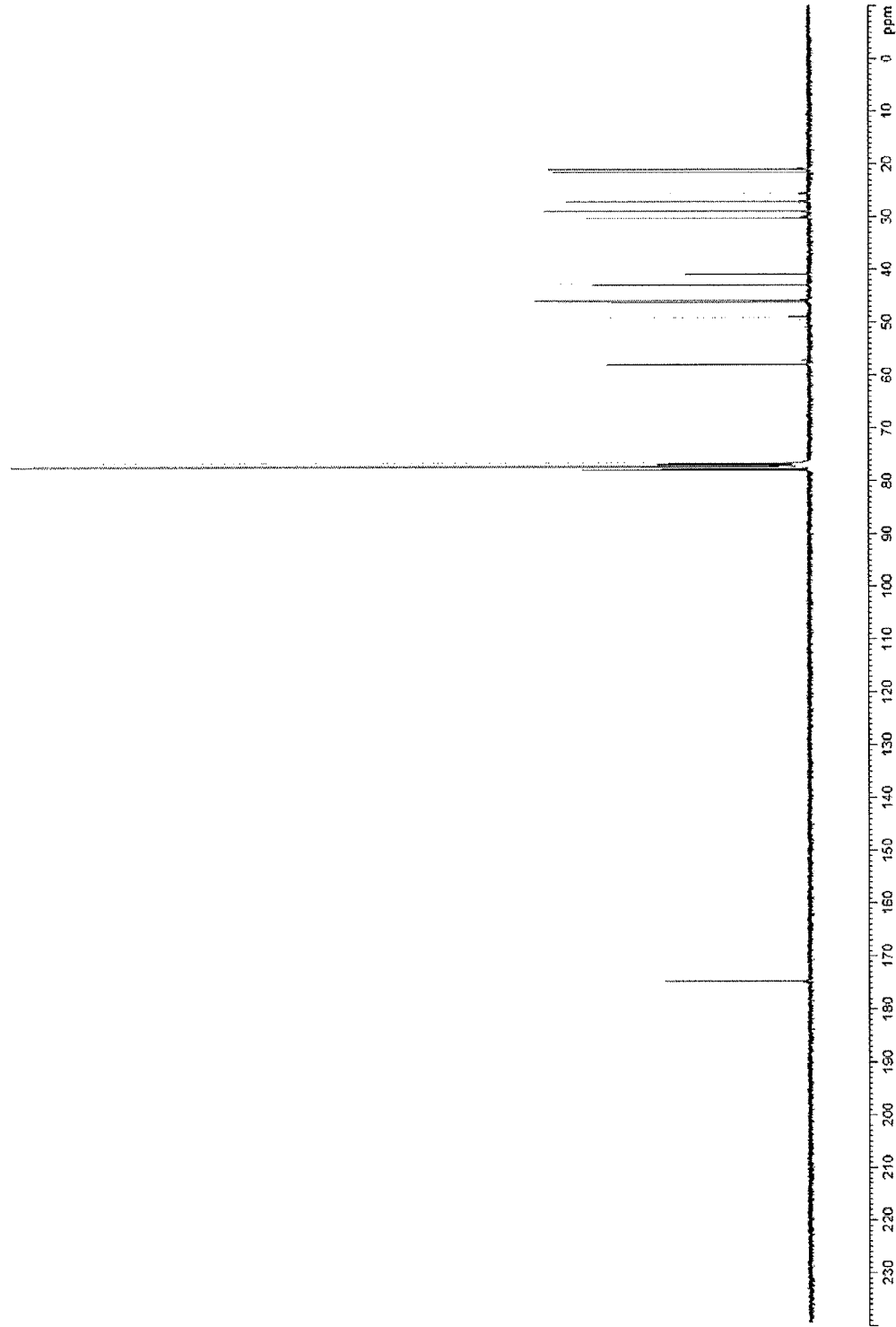
FIG. 2B shows $^{13}$C NMR of the organocatalyst 3b according to the present invention.

At room temperature, the amide compound (4.4 g, 12 mmol) was dissolved in 20 ml of mixed solution of dichloroethane and methanol (volume ratio 10:1), and then NaBH$_4$ (2.3 g, 60 mmol) was added into the mixture and then the mixture was stirred for overnight. The reaction was stopped by ammonium chloride solution, washed by saline solution, dried by magnesium sulfate, filtered and concentrated under reduced pressure to obtain a crude product. The crude product was dissolved in 10 ml of dichloroethane, and then 1 ml of trifluoroacetic acid (TFA) was dropped into the mixture at room temperature. The mixture was stirred for 2 hours, and then diluted with dichloroethane and washed by 2N NaOH. The mixture was then washed by saline solution, dried by magnesium sulfate, filtered, concentrated under reduced pressure, and purified by column chromatography to obtain the organocatalyst 3b. Upon determination, $^1$H NMR and $^{13}$C NMR of the compound 3b were shown in FIG. 2A and FIG. 2B, respectively. $^1$H NMR (400 MHz, CDCl$_3$): δ 6.81 (s, 1H), 4.02 (dd, J=7.8 and 3.5 Hz, 1H), 3.68 (br, s, 2H), 3.57-3.46 (m, 1H), 3.38-3.25 (m, 1H), 3.17-2.98 (m, 1H), 2.91 (t, J=6.8 Hz, 2H), 2.19-1.98 (m, 1H), 1.97-1.88 (m, 2H), 1.86-1.60 (m, 5H), 1.49-1.32 (m, 1H), 1.32-1.19 (m, 4H), 1.16-1.04 (m, 1H), 1.03 (s, 3H); $^{13}$C NMR (100 MHz, CDCl$_3$): δ 174.8, 77.9, 58.1, 58.0, 49.0, 46.2, 45.9, 43.0, 41.0, 30.2, 29.0, 27.0, 25.5, 21.6, 21.0; IR (neat): ν 3271, 2953, 2725, 1634, 1557 cm$^{-1}$; HRMS (FAB$^+$) m/z (MH$^+$)=267.2706 (C$_{15}$H$_{27}$N$_2$O$_2$ calculated as 267.2703); [α]$^{33}_D$+16.49 (c 1.00, CHCl$_3$); m.p. 140-142° C.; 3b crystal data at 296(2)K: C$_{15}$H$_{26}$N$_2$O$_2$, M 266.38; monoclinic crystal, P2$_1$; a=8.0727(3) Å, b=9.2759(4) Å, c=10.3149(4) Å; α=90.00, β=96.558(2), γ=90.00; V=767.34(5) Å3, F000=292; λ(Mo—Kα)=0.71073 Å, Z=2, D=1.153 g/cm$^3$, μ=0.076 mm$^{-1}$, 1389 diffractions, 1 limitation, 173 parameters, R=0.0766, Rw=0.2475

Embodiment 3

Synthesis of a Representative Compound 3c of the Present Invention

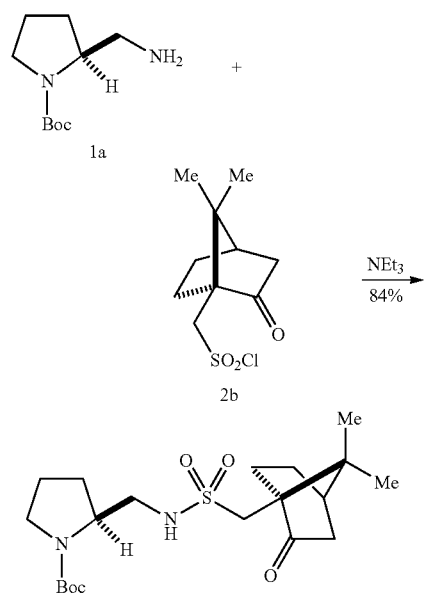

Scheme 3

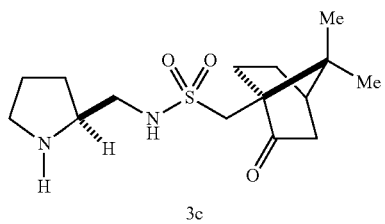

3c

The compound 1a (10.0 g, 49.9 mmol) and the compound 2b (12.9 g, 55.5 mmol) were dissolved in 30 ml of dry dichloromethane. Then, triethylamine (7.2 ml, 51.7 mmol) was added slowly in the mixture at 0° C. The reaction was performed with stirring for 13 hours at room temperature, and stopped with addition of water. The solvent was removed, and the residue was dissolved in 30 ml of dichloromethane and washed with ammonium chloride solution and sodium bicarbonate solution. The mixture was then washed with saline solution and dried by magnesium sulfate. The mixture was filtered and concentrated under reduced pressure, and purified by column chromatography to obtain the sulfonamide compound.

Figure 3A:
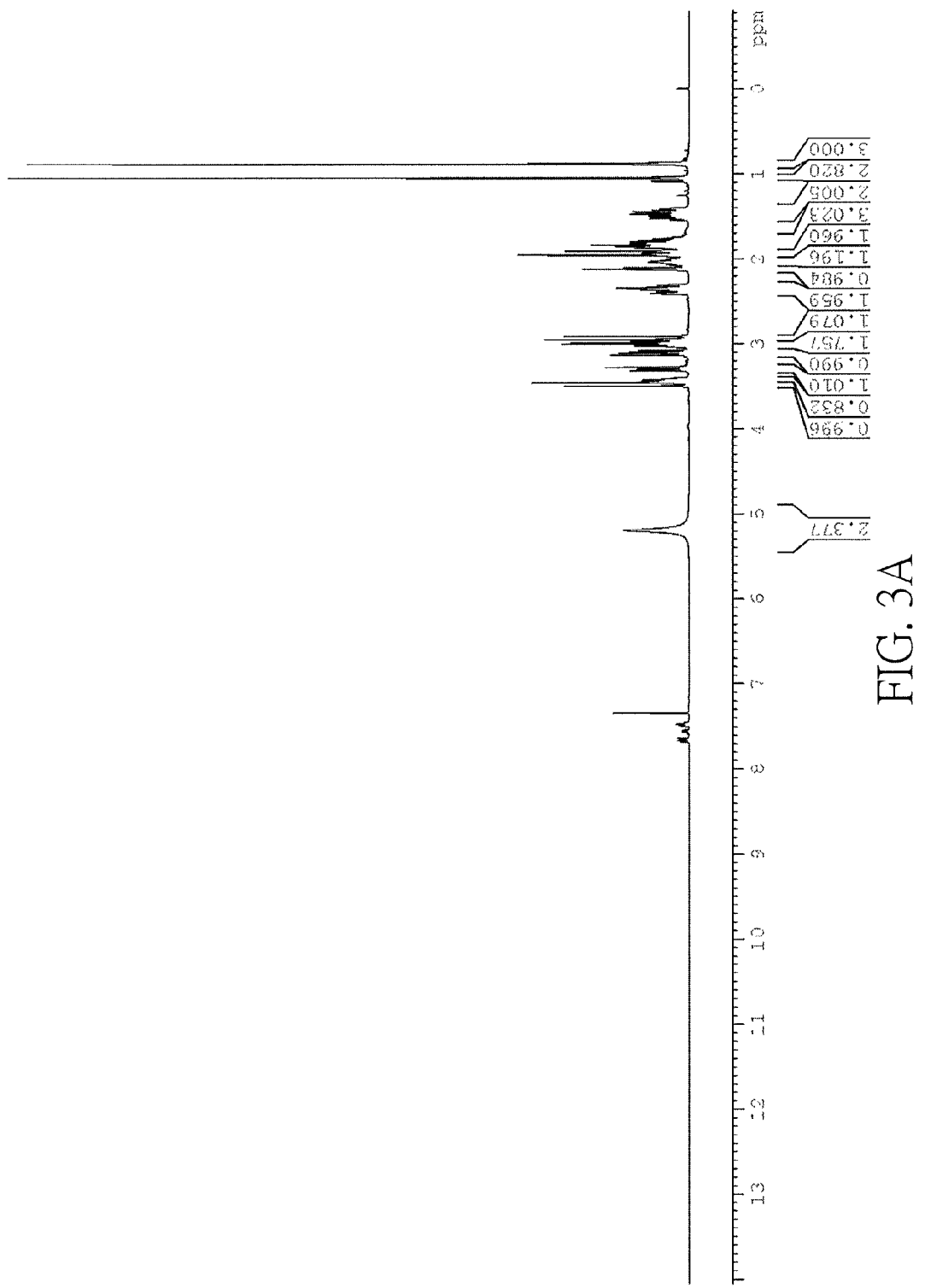
FIG. 3A shows $^1$H NMR of the organocatalyst 3c according to the present invention.
Figure 3B:
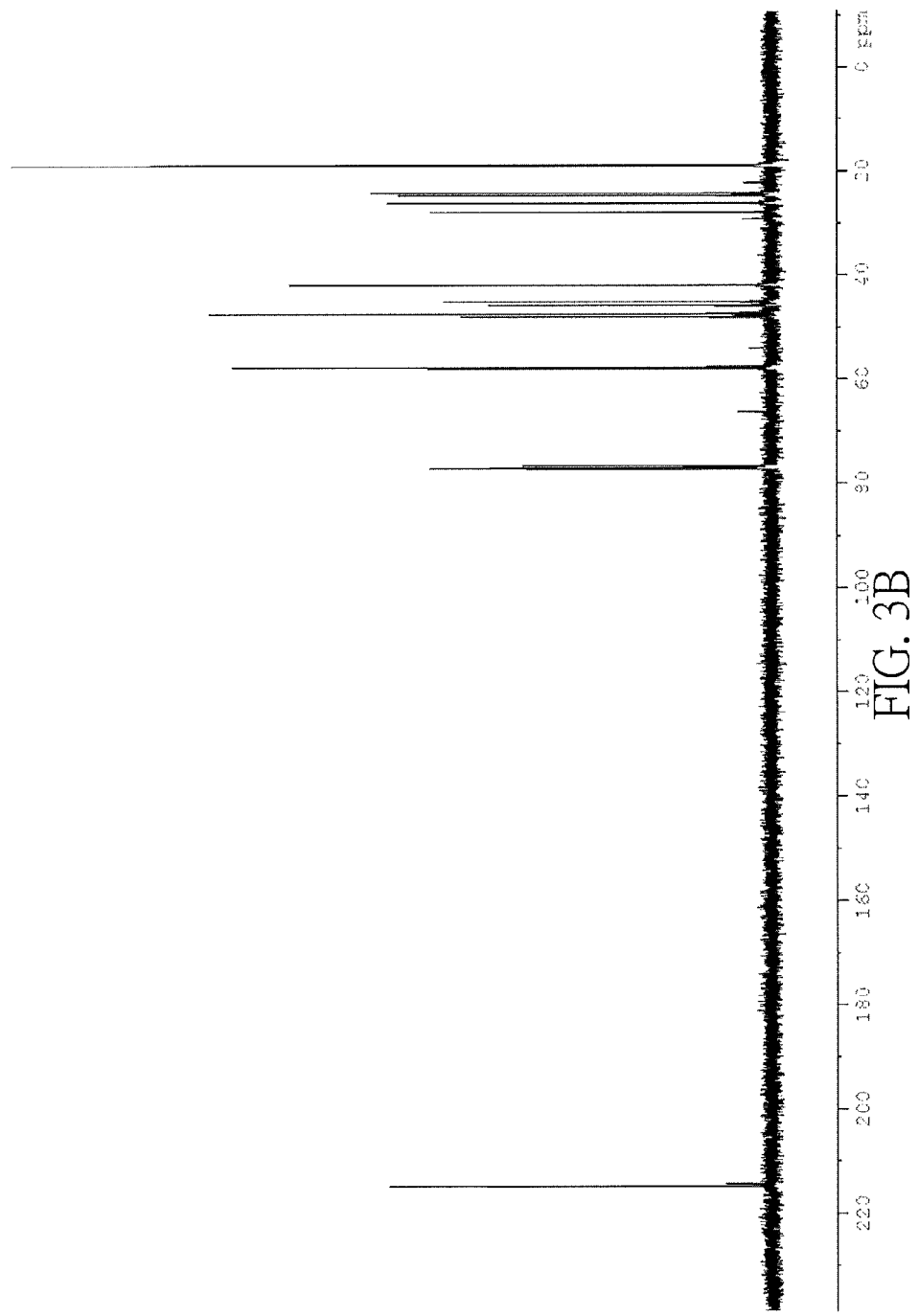
FIG. 3B shows $^{13}$C NMR of the organocatalyst 3c according to the present invention.

The sulfonamide compound was dissolved in 10 ml of dichloromethane, and then 1 ml of trifluoroacetic acid (TFA) was dropped into the mixture at room temperature. The mixture was stirred for 2 hours, and then diluted with sodium bicarbonate solution and washed and adjusted to be basic by dichloromethane. The mixture was then washed by saline solution, dried by magnesium sulfate, filtered, concentrated under reduced pressure, and purified by column chromatography to obtain the organocatalyst 3c. Upon determination, $^1$H NMR and $^{13}$C NMR of the compound 3c were shown in FIG. 3A and FIG. 3B, respectively. $^1$H NMR (400 MHz, CDCl$_3$) δ 5.19 (s, 2H, NH), 3.48 (d, J=15 Hz, 1H), 3.45-3.40 (m, 1H), 3.29 (dd, J=12.92 and 4.24 Hz, 1H), 3.10 (dd, J=12.92 and 8.4 Hz, 1H), 3.03-2.97 (m, 2H), 2.93 (d, J=14.92 Hz, 1H), 2.41-2.30 (m, 2H), 2.12 (t, J=4.32 Hz, 1H), 2.07-2.01 (m, 1H), 1.97-1.90 (m, 2H), 1.87-1.74 (m, 3H), 1.52-1.41 (m, 2H), 1.05 (s, 3H), 0.89 (s, 3H); $^{13}$C NMR (100 MHz, CDCl$_3$) δ 215.0, 58.1, 57.8, 48.0, 47.6, 45.9, 45.1, 42.0, 41.9, 28.0, 26.2, 24.7, 24.3, 19.0, 18.9; HRMS (EI) C$_{15}$H$_{26}$N$_2$O$_3$S calculated as 314.1664; 314.1668

Embodiment 4

Synthesis of a Representative Compound 3d of the Present Invention

Scheme 4

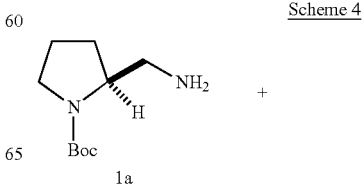

1a

-continued

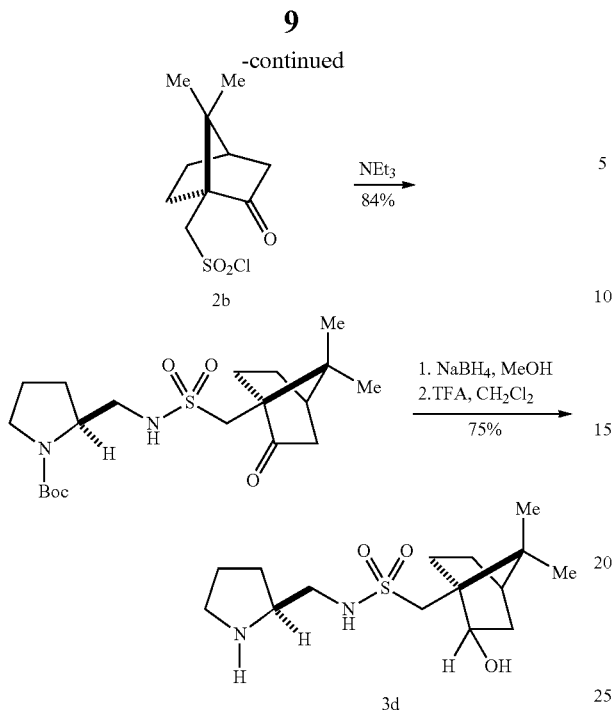

2b

3d

The compound 1a (10.0 g, 49.9 mmol) and the compound 2b (12.9 g, 55.5 mmol) were dissolved in 30 ml of dry dichloromethane. Then, triethylamine (7.2 ml, 51.7 mmol) was added slowly in the mixture at 0° C. The reaction was performed with stirring for 13 hours at room temperature, and stopped with addition of water. The solvent was removed, and the residue was dissolved in 30 ml of dichloromethane and washed with ammonium chloride solution and sodium bicarbonate solution. The mixture was then washed with saline solution and dried by magnesium sulfate. The mixture was filtered and concentrated under reduced pressure, and purified by column chromatography to obtain the sulfonamide compound.

Figure 4A:
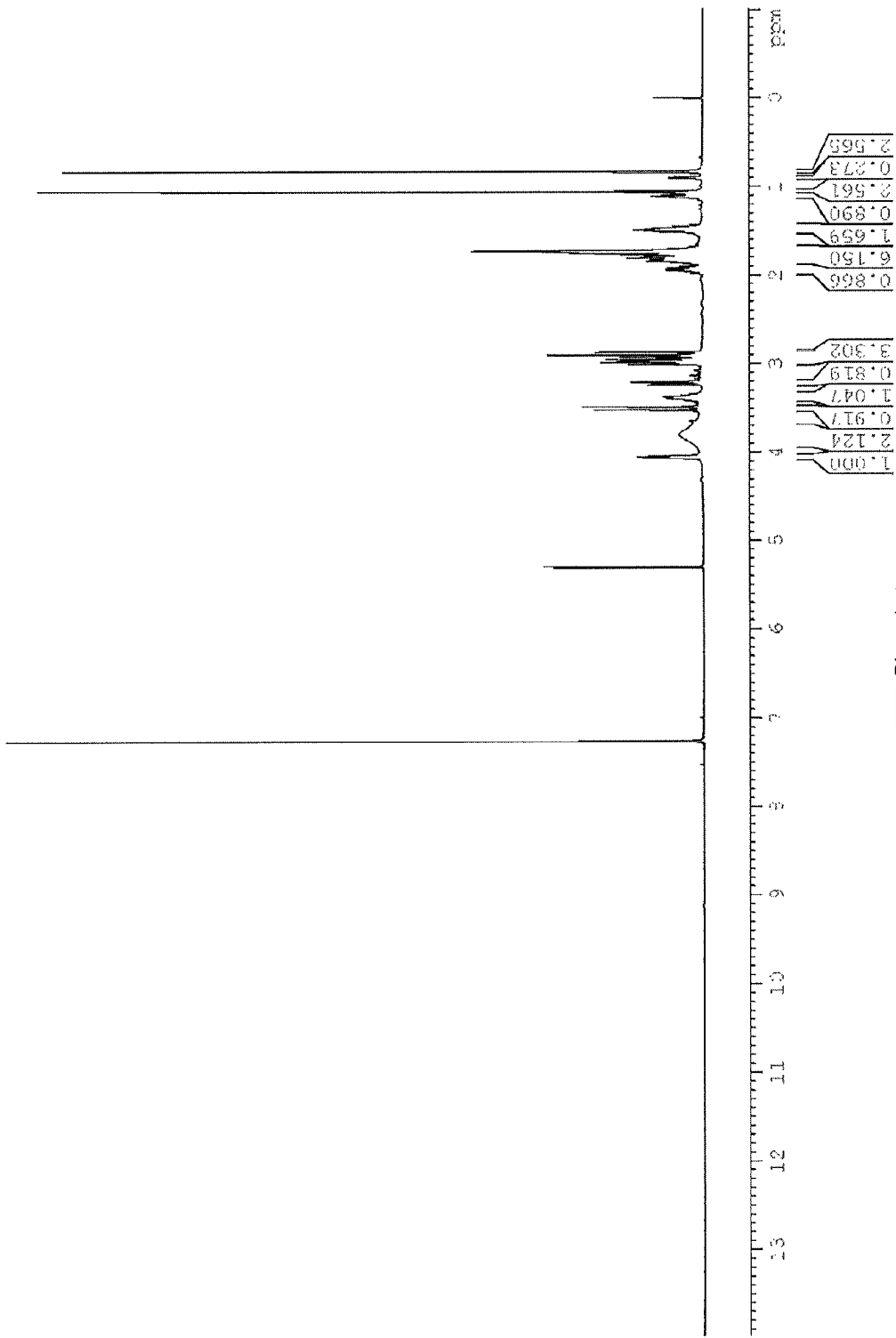
FIG. 4A shows $^1$H NMR of the organocatalyst 3d according to the present invention.
Figure 4B:
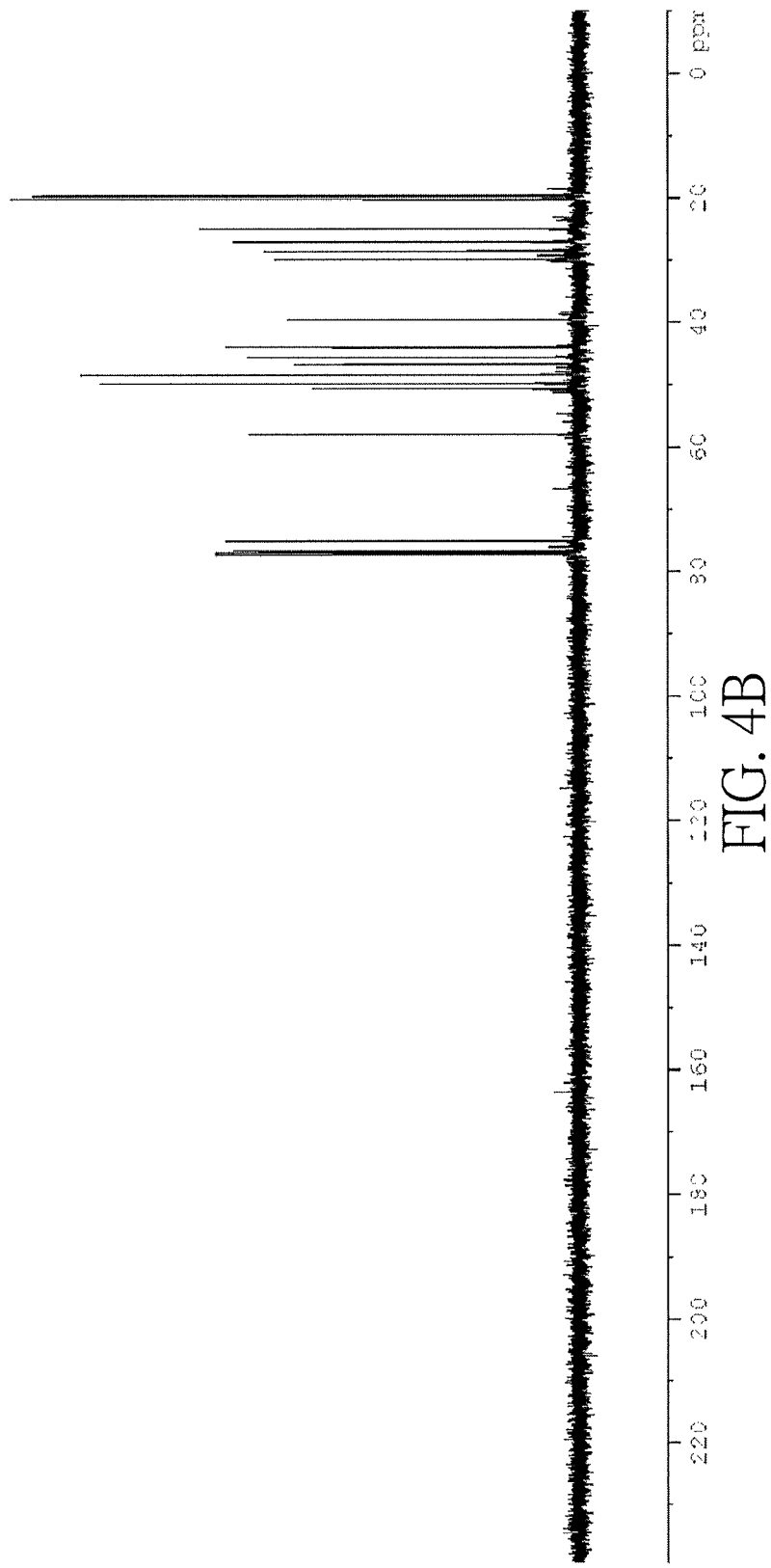
FIG. 4B shows $^{13}$C NMR of the organocatalyst 3d according to the present invention.

The sulfonamide compound (4.975 g, 12 mmol) was dissolved in was dissolved in 20 ml of mixed solution of dichloromethane and methanol (volume ratio 10:1), and then NaBH$_4$ (2.3 g, 60 mmol) was added into the mixture and then the mixture was stirred for overnight. The reaction was stopped by ammonium chloride solution, washed by saline solution, dried by magnesium sulfate, filtered, and concentrated under reduced pressure to obtain a crude product. The crude product was dissolved in 10 ml of dichloromethane, and then 1 ml of trifluoroacetic acid (TFA) was dropped into the mixture at room temperature. The mixture was stirred for 2 hours, and then diluted with sodium bicarbonate solution, and washed and adjusted to be basic by dichloromethane. The mixture was then washed by saline solution, dried by magnesium sulfate, filtered, concentrated under reduced pressure, and purified by column chromatography to obtain the organocatalyst 3d. Upon determination, $^1$H NMR and $^{13}$C NMR of the compound 3d were shown in FIG. 4A and FIG. 4B, respectively. $^1$H NMR (400 MHz, CDCl$_3$) δ 4.05 (dd, J=8.04 and 3.96 Hz, 1H), 3.80 (s, 2H, NH), 3.51 (d, J=13.92 Hz, 1H), 3.44-3.34 (m, 1H), 3.22 (dd, J=12.32 and 3.8 Hz, 1H), 3.00-2.87 (m, 4H), 1.97-1.90 (m, 1H), 1.86-1.65 (m, 7H), 1.51-1.43 (m, 2H), 1.13-1.11 (m, 1H), 1.06 (s, 3H), 0.83 (s, 3H); $^{13}$C NMR (100 MHz, CDCl$_3$) δ 75.1, 58.0, 50.7, 49.8, 48.4, 46.7, 45.6, 44.0, 39.5, 29.9, 28.5, 27.0, 25.0, 20.2, 19.6; HRMS (EI) C$_{15}$H$_{28}$N$_2$O$_3$S calculated as 316.1821; 316.1831

Embodiment 5

Synthesis of a Representative Compound 3e of the Present Invention

Scheme 5

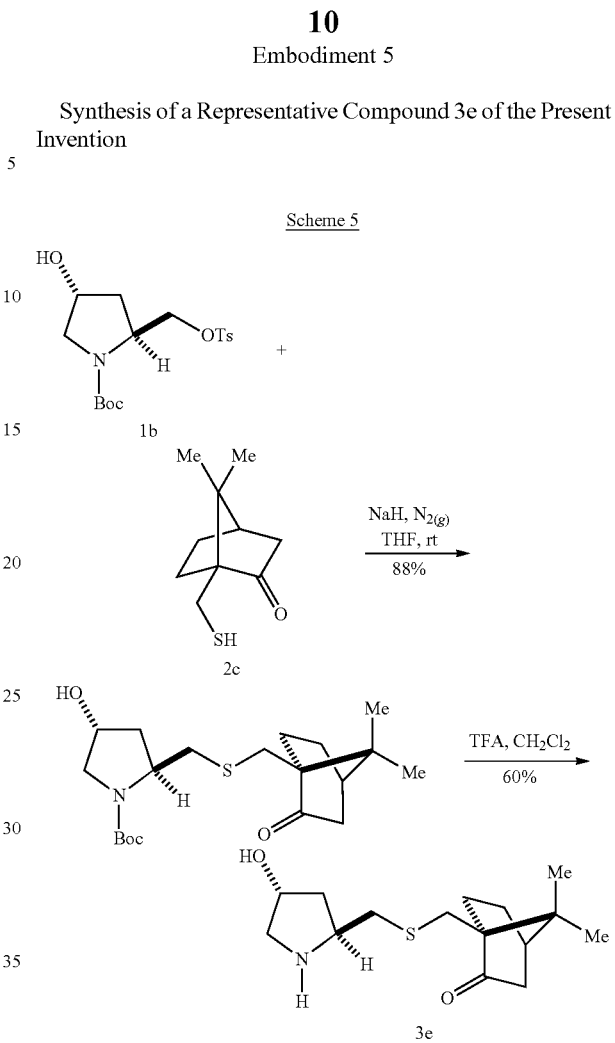

3e

At the atmosphere of nitrogen excluding oxygen, the compound 1b (2.0 g, 5.4 mmol) and the compound 2c (1.5 g, 8.1 mmol) were dissolved in 30 ml of dried tetrahydrofuran, and then sodium hydride (1.5 g, 27 mmol) was added to the mixture at 0° C. At room temperature, the reaction was performed with stirring for 3 hours, and then the solvent was removed. The residue was dissolved in 30 ml of dichloroethane, and washed with ammonium chloride solution and sodium bicarbonate solution. The mixture was then washed with saline solution and dried by magnesium sulfate. The mixture was filtered and concentrated under reduced pressure, and purified by column chromatography to obtain a crude product.

Figure 5A:
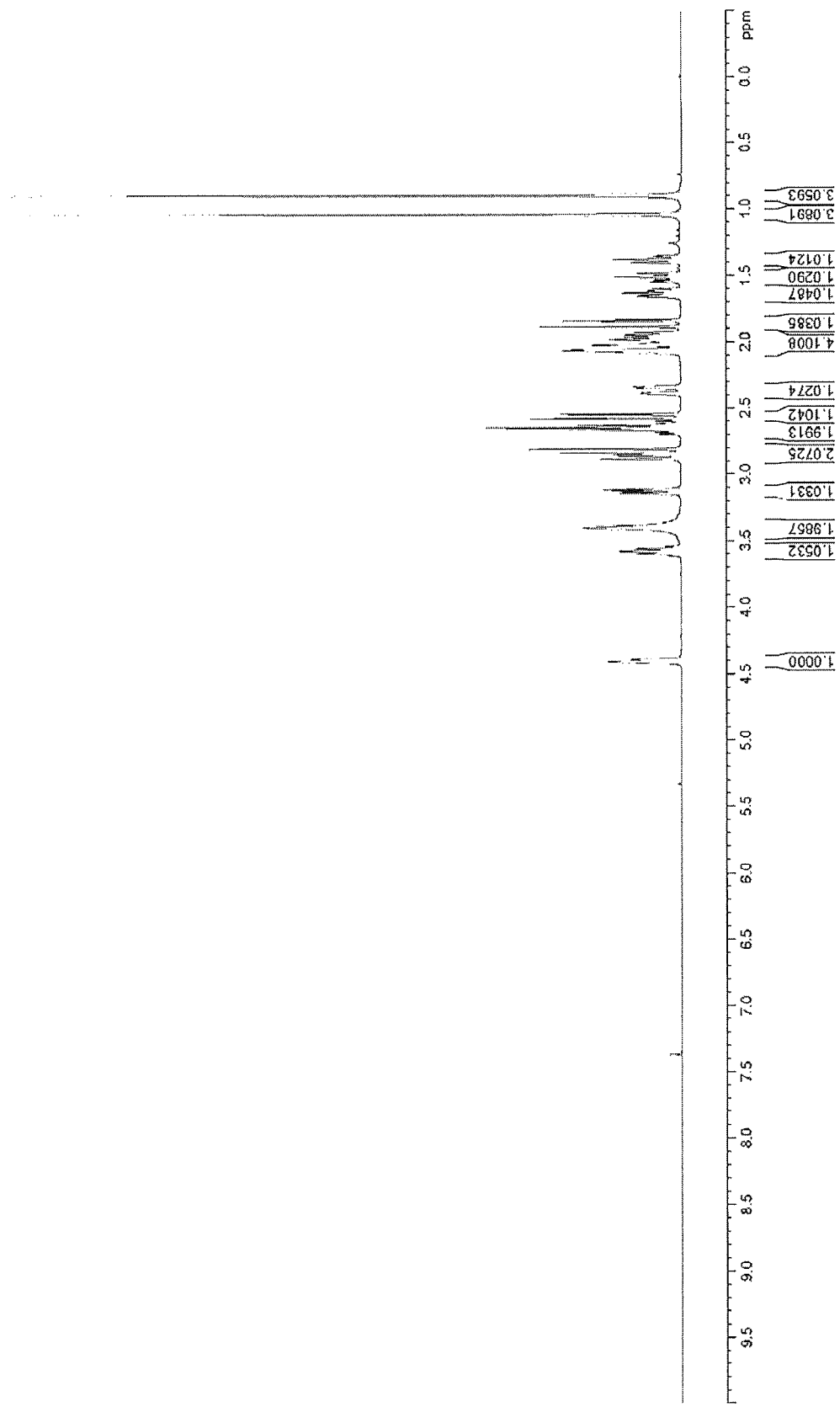
FIG. 5A shows $^1$H NMR of the organocatalyst 3e according to the present invention.
Figure 5B:
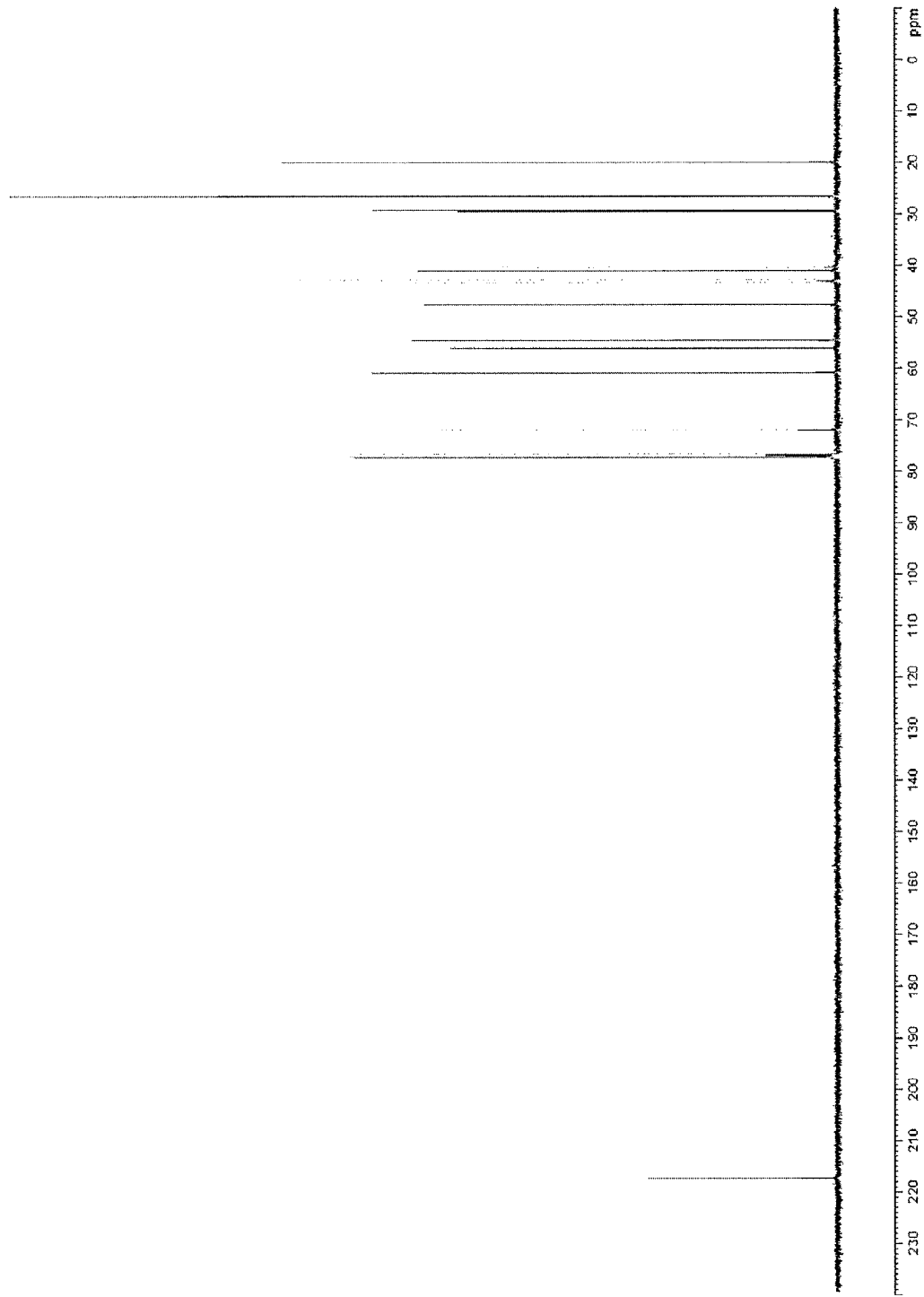
FIG. 5B shows $^{13}$C NMR of the organocatalyst 3e according to the present invention.

The crude product was dissolved in 20 ml of dichloroethane, and then 6 ml of trifluoroacetic acid (TFA) was dropped into the mixture. The mixture was stirred for 3 hours, and diluted with dichloroethane and water. The impurity was removed by dichloroethane. The mixture was neutralized to pH 9 with sodium carbonate solution, and extracted with dichloroethane for several times. The mixture was then washed with saline solution and dried by magnesium sulfate. The mixture was filtered, concentrated under reduced pressure, and purified by column chromatography to obtain the organocatalyst 3e of the present invention. Upon determination, $^1$H NMR and $^{13}$C NMR of the compound 3e were shown in FIG. 5A and FIG. 5B, respectively. $^1$H NMR (400 MHz, CDCl$_3$) δ 4.40 (t, J=10.2 and 5.2 Hz, 1H), 3.61-3.54 (m, 1H), 3.40 (s, 2H), 3.11 (dd, J=11.6 and 4.7 Hz, 1H), 2.87 (d, J=11.7 Hz, 1H), 2.82 (d, J=13.0 Hz, 1H), 2.70-2.60 (m, 2H), 2.57 (d, J=13.0 Hz, 1H), 2.39 (dq, J=4.3 and 2.6 Hz, 1H), 2.09-1.93 (m, 4H), 1.86 (d, J=18.3 Hz, 1H), 1.67-1.60 (m, 1H), 1.55-1.49 (m, 1H), 1.41-1.35 (m, 1H), 1.05 (s, 3H), 0.90 (s, 3H); $^{13}$C NMR (100 MHz, CDCl$_3$) δ 217.4, 71.9, 60.8, 56.1, 54.6, 47.6, 43.2, 42.9, 41.1, 40.3, 29.4, 26.6, 20.0, 19.9; IR (CH$_2$Cl$_2$) ν 3424, 2959, 2886, 1738, 1650, 1414 cm$^{-1}$; m.p. 95-100° C.; HRMS (EI) C$_{15}$H$_{25}$NO$_2$S calculated as 283.1606; 283.1608; [α]$^{33}_D$+34.3 (c 1.00, CHCl$_3$); 3e crystal data at 200(2) K: C$_{15}$H$_{25}$NO$_2$S, M 283.42, monoclinic crystal, P2$_1$2$_1$2$_1$, a=9.0657(2) Å, b=10.6218(2) Å, c=31.5723(7) Å, V=3040.23(11) Å$^3$, Z=8, Dx=1.238 Mg/m$^3$, μ=0.212 mm$^{-1}$, 19384 diffractions, 0 limitation, 343 parameters, R=0.0939, Rw=0.1509

Embodiment 6

Synthesis of a Representative Compound 3f of the Present Invention

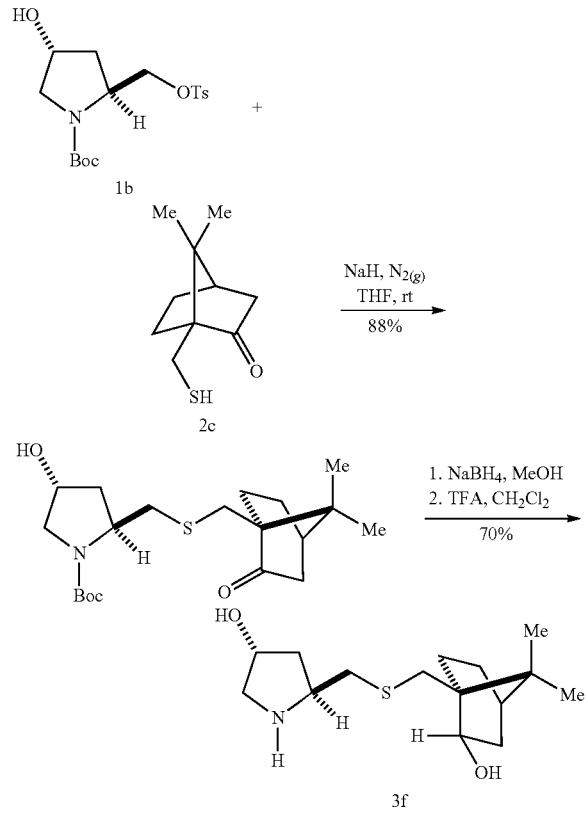

Figure 6A:
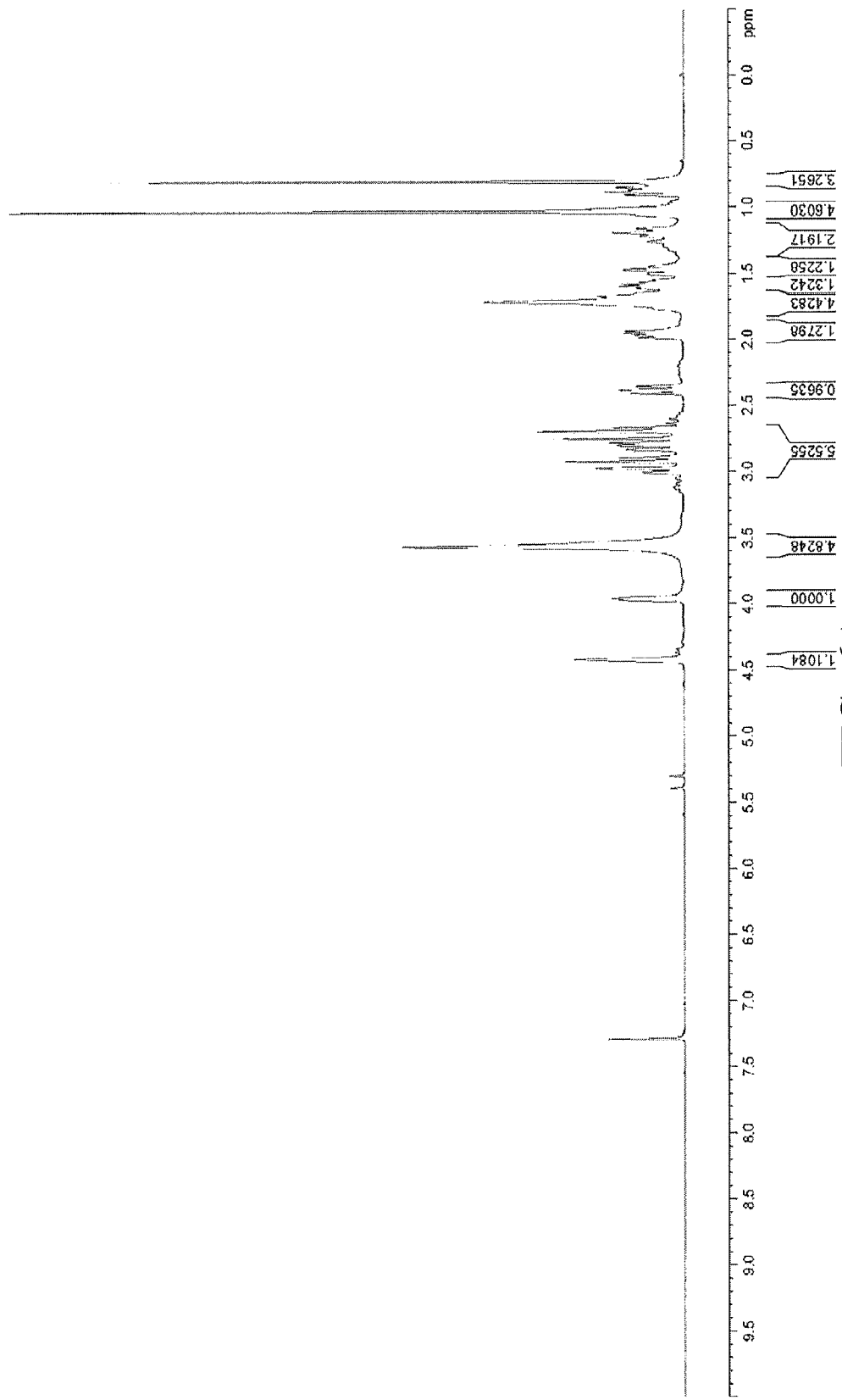
FIG. 6A shows $^1$H NMR of the organocatalyst 3f according to the present invention.
Figure 6B:
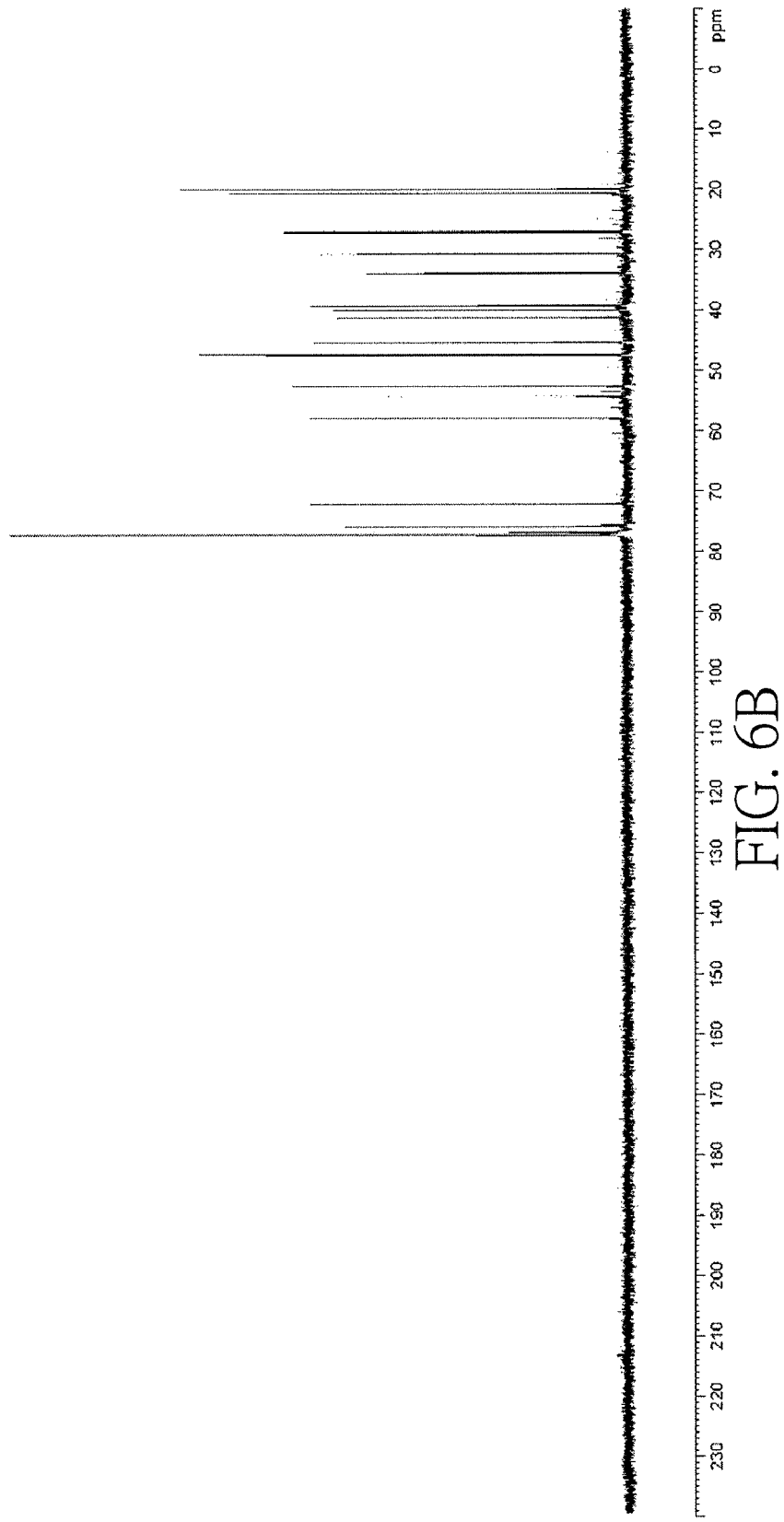
FIG. 6B shows $^{13}$C NMR of the organocatalyst 3f according to the present invention.

At room temperature, the crude product (1.5 g, 3.9 mmol) of embodiment 5 was dissolved in 20 ml of mixed solution of dichloromethane and methanol (volume ratio 10:1), and then NaBH$_4$ (0.75 g, 20 mmol) was added into the mixture. The reaction was performed with stirring for 1 hour and then the reaction was stopped by ammonium chloride solution. The mixture was washed by saline solution, dried by magnesium sulfate, filtered, and concentrated under reduced pressure to obtain a crude product. The crude product was dissolved in 20 ml of dichloroethane, and then 6 ml of trifluoroacetic acid (TFA) was dropped into the mixture at room temperature. The mixture was stirred for 3 hours, and then diluted with dichloroethane and water. The impurity was removed by dichloroethane. Then, the mixture was neutralized to pH 9 by sodium carbonate solution. The mixture was extracted with dichloroethane for several times. The mixture was then washed by saline solution, dried by magnesium sulfate, filtered, and concentrated under reduced pressure to obtain the organocatalyst 3f. Upon determination, $^1$H NMR and $^{13}$C NMR of the compound 3f were shown in FIG. 6A and FIG. 6B, respectively. $^1$H NMR (400 MHz, CDCl$_3$) δ 4.42 (s, 1H), 3.96 (s, 1H), 3.56 (s, 4H), 2.98-2.67 (m, 5H), 2.38 (t, J=11.6 Hz, 1H), 1.99-1.94 (m, 1H), 1.72-1.65 (m, 4H), 1.61-1.55 (m, 1H), 1.50-1.45 (m, 1H), 1.32-1.16 (m, 2H), 1.04 (s, 3H), 0.81 (s, 3H); $^{13}$C NMR (100 MHz, CDCl$_3$) δ 75.7, 72.1, 57.8, 54.2, 52.5, 47.3, 45.2, 41.2, 39.9, 39.3, 33.8, 30.7, 27.0, 20.6, 19.9; IR (CH$_2$Cl$_2$) ν 3392, 2903, 1646, 1428 cm$^{-1}$; HRMS (EI) C$_{15}$H$_{27}$NO$_2$S calculated as 285.1762; 285.1768; [α]$^{33}_D$−2.5 (c 1.00, CHCl$_3$); 3f crystal data at 200(2) K: C$_{15}$H$_{28}$ClNO$_2$S, M 321.89, monoclinic crystal, P2$_1$, a=21.970(6) Å, b=6.7270 (17) Å, c=22.818(6) Å, V=3339.1(15) Å$^3$, Z=8, Dx=1.281 Mg/m$^3$, μ=0.356 mm$^{-1}$, 24315 diffractions, 1 limitation, 415 parameters, R=0.1938, Rw=0.2920

Embodiment 7

Synthesis of a Representative Compound 3g of the Present Invention

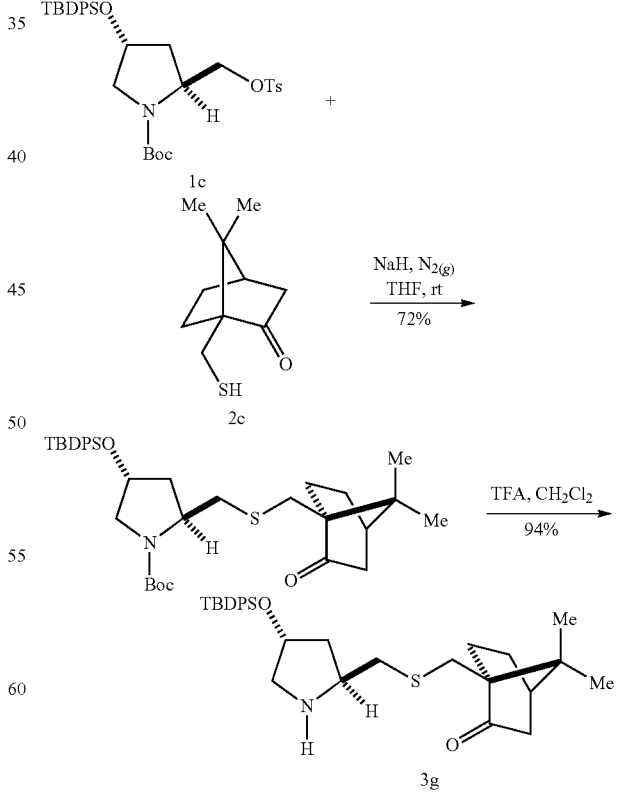

At the atmosphere of nitrogen excluding oxygen, the compound 1c (5.0 g, 8.2 mmol), which was obtained from the reaction of tert-butyl diphenylchlorosilaneb (TBDPSCl) and the compound 1b in the presence of triethylamine and DMAP at room temperature for 2 days) and the compound 2c (2.0 g, 9.8 mmol) were dissolved in 30 ml of dried tetrahydrofuran, and then sodium hydride (3.0 g, 41 mmol) was added to the mixture at 0° C. At room temperature, the reaction was performed with stirring for 2 hours, and then the solvent was removed. The residue was dissolved in 30 ml of dichloroethane, and washed with ammonium chloride solution and sodium bicarbonate solution. The mixture was then washed with saline solution and dried by magnesium sulfate. The mixture was filtered and concentrated under reduced pressure, and purified by column chromatography to obtain a crude product.

Figure 7A:
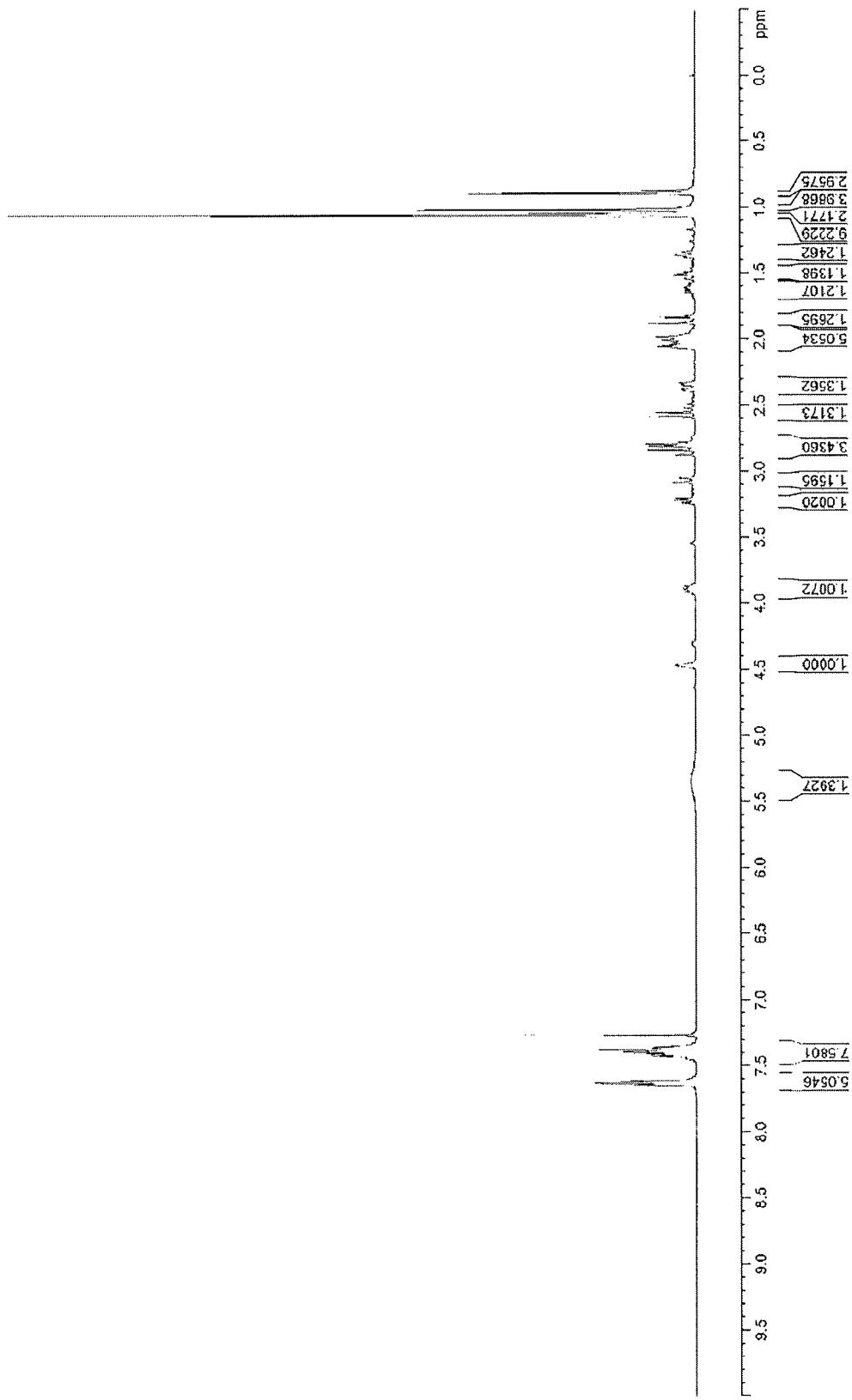
FIG. 7A shows $^1$H NMR of the organocatalyst 3g according to the present invention.
Figure 7B:
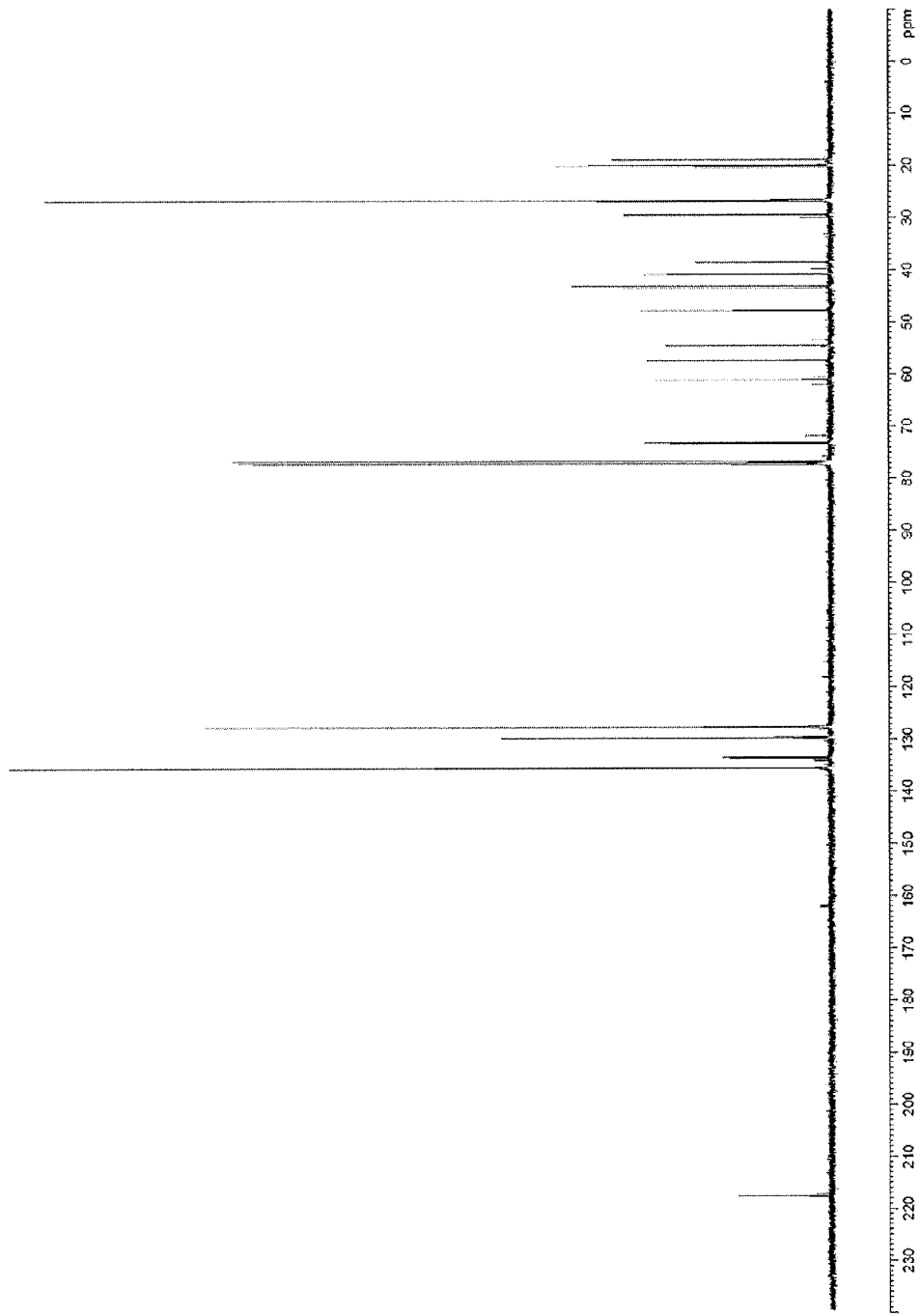
FIG. 7B shows $^{13}$C NMR of the organocatalyst 3g according to the present invention.

The crude product was dissolved in 20 ml of dichloroethane, and then 1 ml of trifluoroacetic acid (TFA) was dropped into the mixture. The mixture was stirred for 1 hour, and diluted with dichloroethane and water. The mixture was neutralized to pH 9 with sodium carbonate solution, and extracted with dichloroethane for several times. The mixture was then washed with saline solution and dried by magnesium sulfate. The mixture was filtered, and concentrated under reduced pressure to obtain the organocatalyst 3g of the present invention. Upon determination, $^1$H NMR and $^{13}$C NMR of the compound 3e were shown in FIG. 7A and FIG. 7B, respectively. $^1$H NMR (400 MHz, CDCl$_3$) δ 7.65-7.61 (m, 4H), 7.43-7.36 (m, 6H), 5.35 (br, 1H, NH), 4.48-4.46 (m, 1H), 3.93-3.85 (m, 1H), 3.22 (dd, J=12.0 and 4.8 Hz, 1H), 3.07 (d, J=11.9 Hz, 1H), 2.86 (d, J=13.2 Hz, 1H), 2.81-2.77 (m, 2H), 2.57 (d, J=13.2 Hz, 1H), 2.36 (dq, J=4.6 and 2.1 Hz, 1H), 2.06-1.96 (m, 4H), 1.86 (d, J=18.4 Hz, 1H), 1.65-1.57 (m, 1H), 1.54-1.49 (m, 1H), 1.38-1.34 (m, 1H), 1.06 (s, 9H), 1.02 (s, 3H), 0.90 (s, 3H); $^{13}$C NMR (100 MHz, CDCl$_3$) δ 217.5, 135.5, 133.5, 129.71, 127.7, 73.2, 61.0, 57.4, 54.5, 47.7, 43.5, 43.0, 40.8, 38.4, 29.4, 26.9, 26.8, 20.1, 20.0, 18.9; IR (CH$_2$Cl$_2$) ν 3478, 3070, 2967, 2856, 1742, 1683, 1591, 1429 cm$^{-1}$; HRMS (EI) C$_{31}$H$_{43}$NO$_2$Ssi calculated as 521.2784; 521.2782; [α]$^{33}_D$+3.9 (c 1.00, CHCl$_3$)

Embodiment 8

Synthesis of a Representative Compound 3h of the Present Invention

Scheme 8

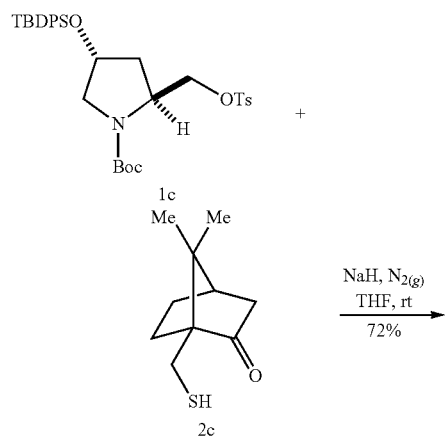

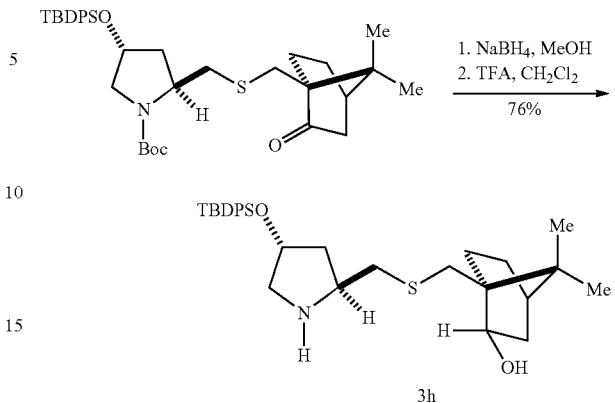

Figure 8A:
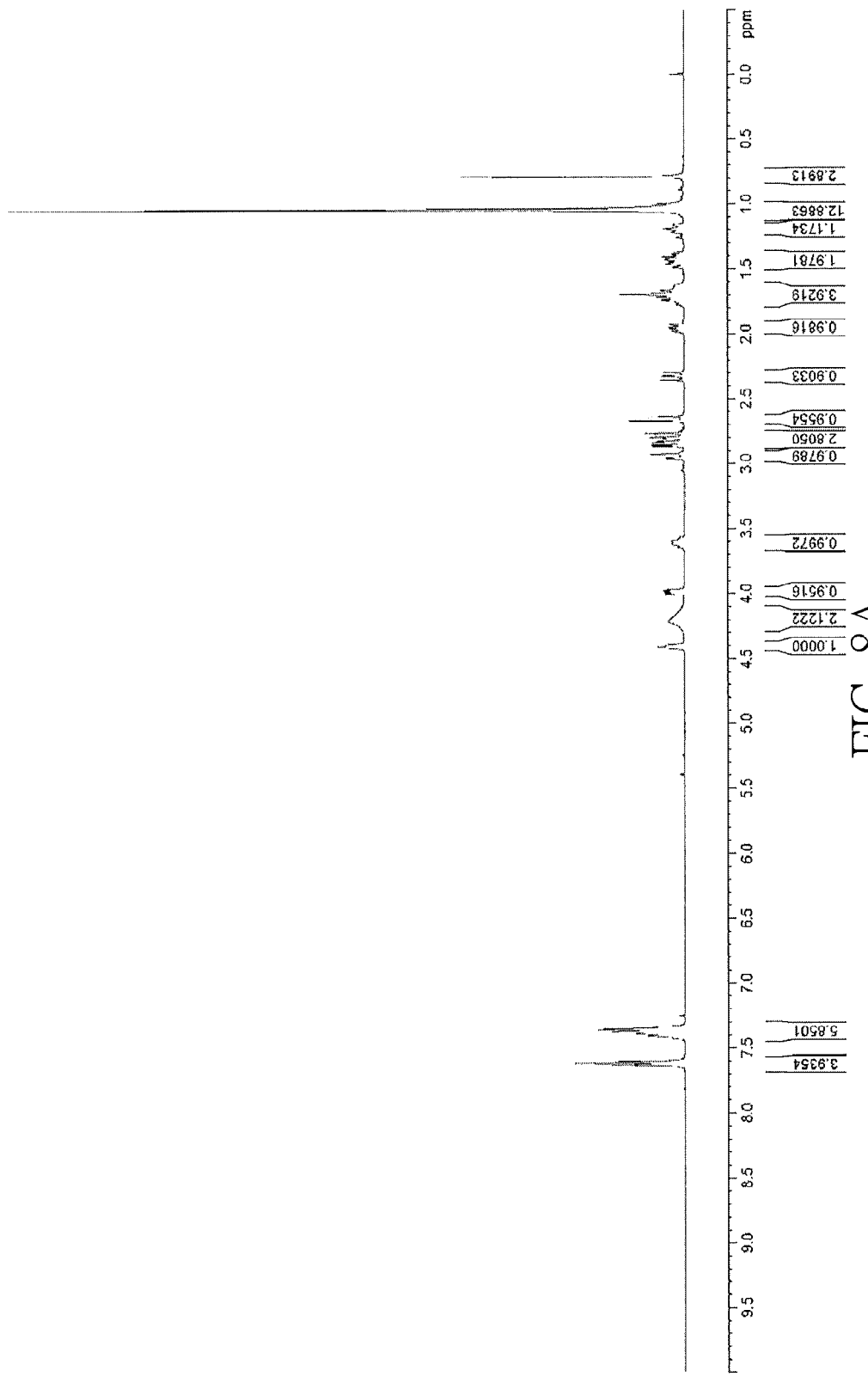
FIG. 8A shows $^1$H NMR of the organocatalyst 3h according to the present invention.
Figure 8B:
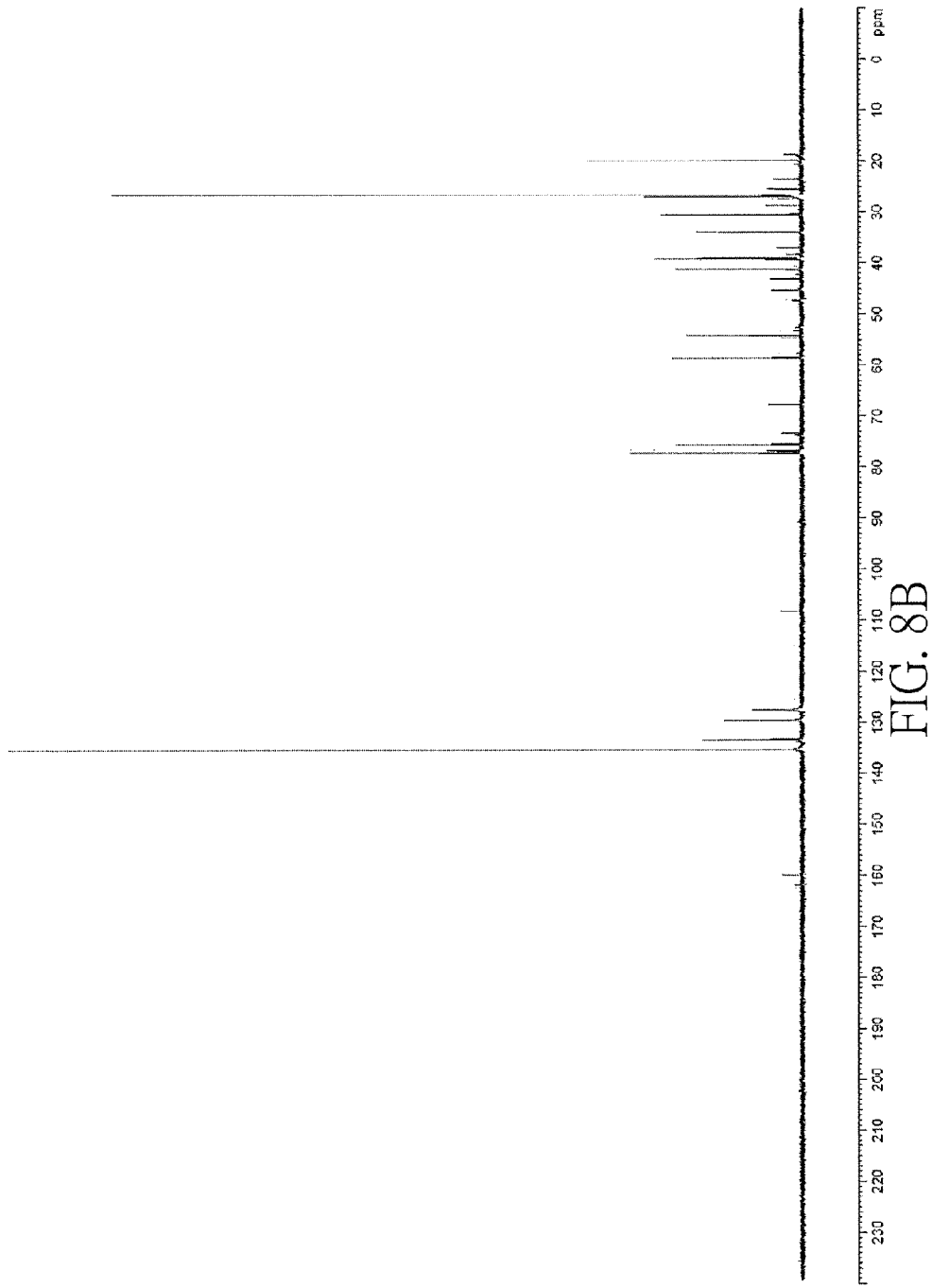
FIG. 8B shows $^{13}$C NMR of the organocatalyst 3h according to the present invention.

At room temperature, the crude product (1.0 g, 1.6 mmol) of embodiment 7 was dissolved in 20 ml of mixed solution of dichloroethane and methanol (volume ratio 1:1), and then NaBH$_4$ (0.3 g, 8 mmol) was added into the mixture. The reaction was performed with stirring for 3 hours and then the reaction was stopped by ammonium chloride solution. The mixture was washed by saline solution, dried by magnesium sulfate, filtered, and concentrated under reduced pressure to obtain a crude product. The crude product was dissolved in 10 ml of dichloroethane, and then 1 ml of trifluoroacetic acid (TFA) was dropped into the mixture at room temperature. The mixture was stirred for 1 hour, and then diluted with dichloroethane and water. Then, the mixture was neutralized to pH 9 by sodium carbonate solution. The mixture was extracted with dichloroethane for several times. The mixture was then washed by saline solution, dried by magnesium sulfate, filtered, and concentrated under reduced pressure to obtain the organocatalyst 3h. Upon determination, $^1$H NMR and $^{13}$C NMR of the compound 3h were shown in FIG. 8A and FIG. 8B, respectively. $^1$H NMR (400 MHz, CDCl$_3$) δ 7.64-7.60 (m, 4H), 7.41-7.34 (m, 6H), 4.41 (t, J=4.6 Hz, 1H), 4.21 (s, 2H), 3.99 (q, J=7.8 and 3.9 Hz, 1H), 3.63-3.58 (m, 1H), 2.94 (d, J=12.2 Hz, 1H), 2.87-2.77 (m, 3H), 2.66 (d, J=11.7 Hz, 1H), 2.33 (q, J=13.6 and 9.9 Hz, 1H), 1.96 (q, J=13.6 and 7.0 Hz, 1H), 1.79-1.64 (m, 4H), 1.49-1.38 (m, 2H), 1.22-1.16 (m, 1H), 1.05 (s, 9H), 1.03 (s, 3H), 0.79 (s, 3H); $^{13}$C NMR (100 MHz, CDCl$_3$) δ 135.4, 133.5, 129.6, 127.5, 75.5, 73.7, 58.5, 54.2, 53.2, 52.5, 47.2, 45.2, 41.2, 39.2, 33.9, 30.5, 26.9, 26.7, 20.5, 19.8, 18.8; IR (CH$_2$Cl$_2$) ν 3373, 3077, 2959, 1679, 1591, 1469 cm$^{-1}$; HRMS (EI) C$_{31}$H$_{45}$NO$_2$Ssi calculated as 523.2940; 523.2950; [α]$^{33}_D$+5.6 (c 1.00, CHCl$_3$); 3h crystal data at 200(2) K: C$_{31}$H$_{46}$ClNO$_2$SSi, M 560.29, monoclinic crystal, P2$_1$2$_1$2$_1$, a=7.4564(2) Å, b=17.4817(4) Å, c=24.0121 (10) Å, V=3129.99(17) Å$^3$, Z=4, Dx=1.189 Mg/m$^3$, μ=0.254 mm$^{-1}$, 7875 diffractions, 0 limitation, 334 parameters, R=0.0628, Rw=0.1301

Embodiment 9

Synthesis of a Representative Compound 3i of the Present Invention

Scheme 9

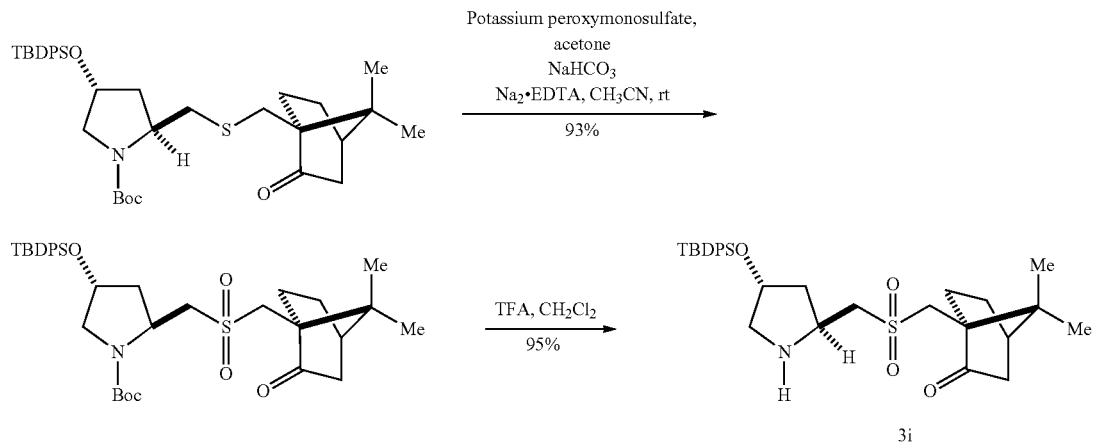

Figure 9A:
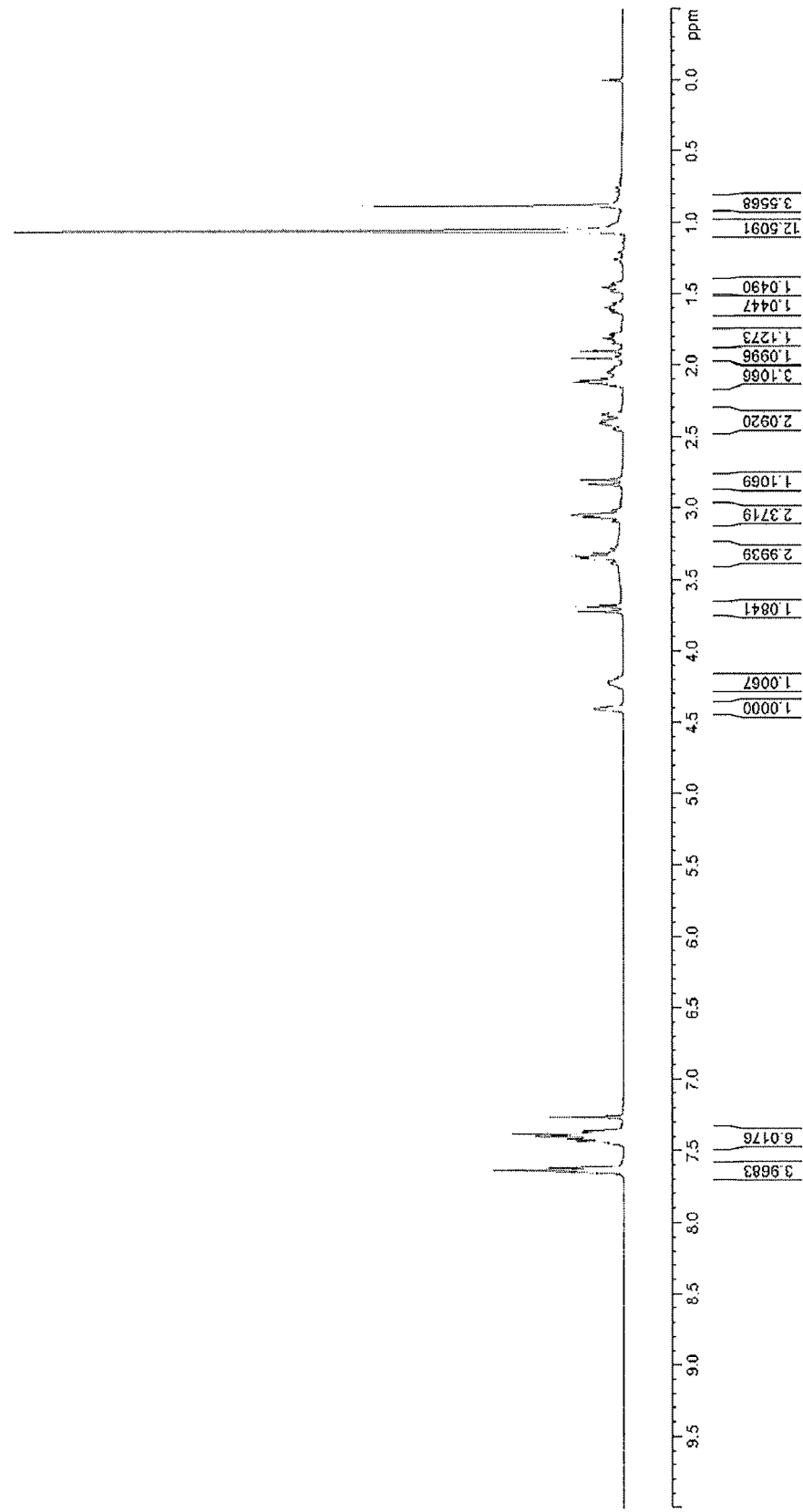
FIG. 9A shows $^1$H NMR of the organocatalyst 3i according to the present invention.
Figure 9B:
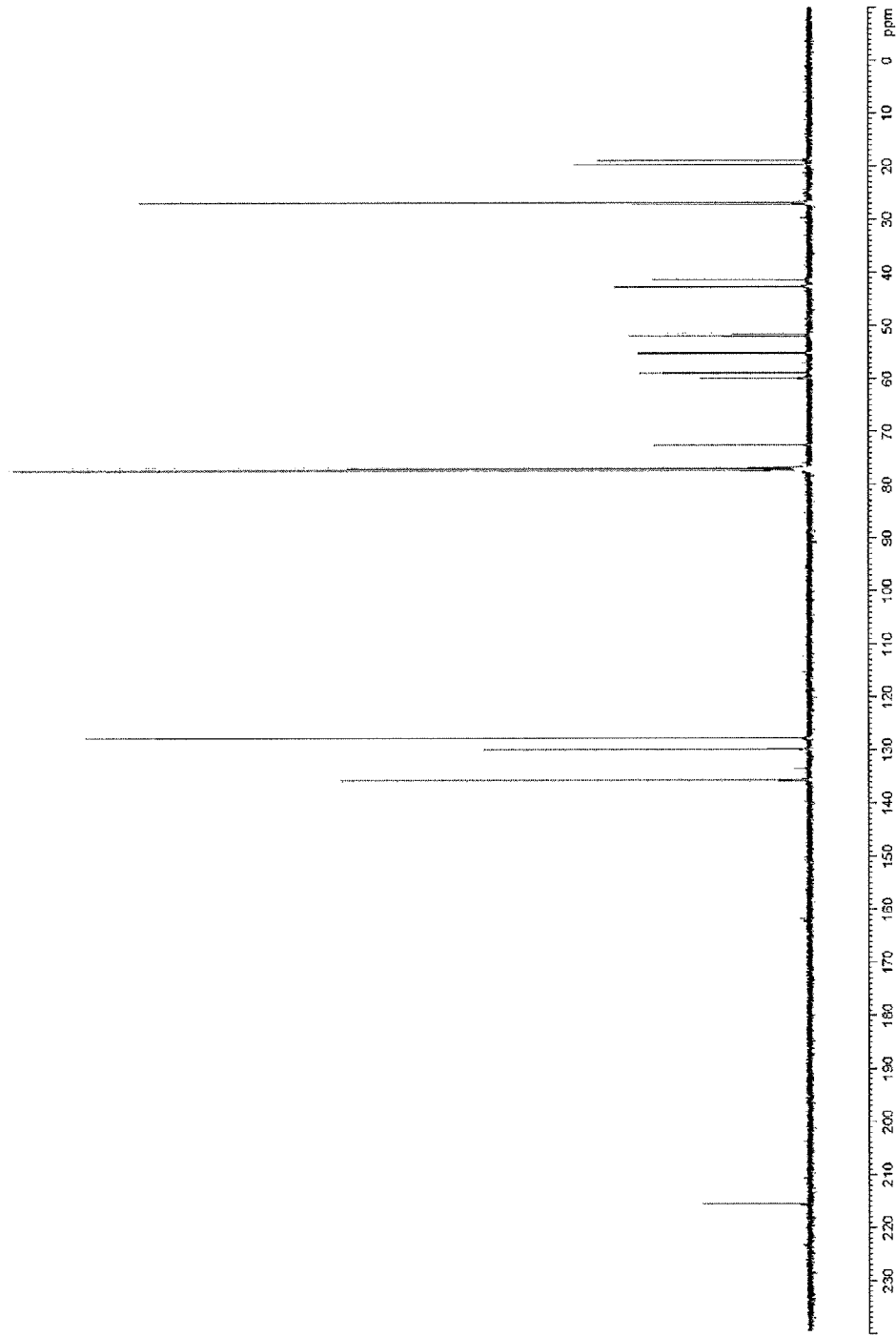
FIG. 9B shows $^{13}$C NMR of the organocatalyst 3i according to the present invention.

At room temperature, the crude product (1.0 g, 1.6 mmol) of embodiment 7 was dissolved in 60 ml of CH$_3$CN and 40 ml of Na$_2$.EDTA, and 20 ml of acetone was added into the mixture with stirring. Potassium peroxymonosulfate (2.0 g, 3.2 mmol) and sodium bicarbonate (0.82 g, 9.6 mmol) were added to the mixture. The reaction was performed with stirring for 30 minutes, and then stopped by ammonium chloride solution. The mixture was then washed by saline solution, dried by magnesium sulfate, filtered, and concentrated under reduced pressure to obtain a crude product. The crude product was dissolved in 10 ml of dichloroethane, and then 1 ml of trifluoroacetic acid (TFA) was dropped into the mixture at room temperature. The mixture was stirred for 1 hour, and then diluted with dichloroethane. Then, the mixture was washed with sodium carbonate solution. The mixture was then washed by saline solution, dried by magnesium sulfate, filtered, concentrated under reduced pressure, and purified by column chromatography to obtain the organocatalyst 3i. Upon determination, $^1$H NMR and $^{13}$C NMR of the compound 3i were shown in FIG. 9A and FIG. 9B, respectively. $^1$H NMR (400 MHz, CDCl$_3$) δ 7.65-7.61 (m, 4H), 7.44-7.38 (m, 6H), 4.25-4.18 (m, 1H), 3.70 (d, J=14.9 Hz, 1H), 3.37-3.32 (m, 2H), 3.10-3.01 (m, 2H), 2.82 (d, J=15.0 Hz, 1H), 2.45-2.34 (m, 3H), 2.13-2.04 (m, 3H), 1.93 (d, J=18.5 Hz, 1H), 1.85-1.78 (m, 1H), 1.64-1.57 (m, 1H), 1.49-1.43 (m, 1H), 1.06 (s, 12H), 0.88 (s, 3H); $^{13}$C NMR (100 MHz, CDCl$_3$) δ 215.5, 135.6, 133.6, 129.8, 127.7, 72.5, 59.8, 58.8, 55.1, 51.9, 51.4, 48.7, 42.6, 42.5, 41.3, 27.1, 26.8, 24.9, 19.7, 19.6, 19.0; IR (CH$_2$Cl$_2$) v 3365, 3063, 2930, 2886, 1746, 1683, 1587, 1429 cm$^{-1}$; HRMS (EI) C$_{31}$H$_{43}$NO$_4$Ssi calculated as 553.2682; 553.2689; [α]$^{33}_D$+10.1 (c 0.50, CHCl$_3$)

Embodiment 10

Synthesis of a Representative Compound 3j of the Present Invention

Scheme 10

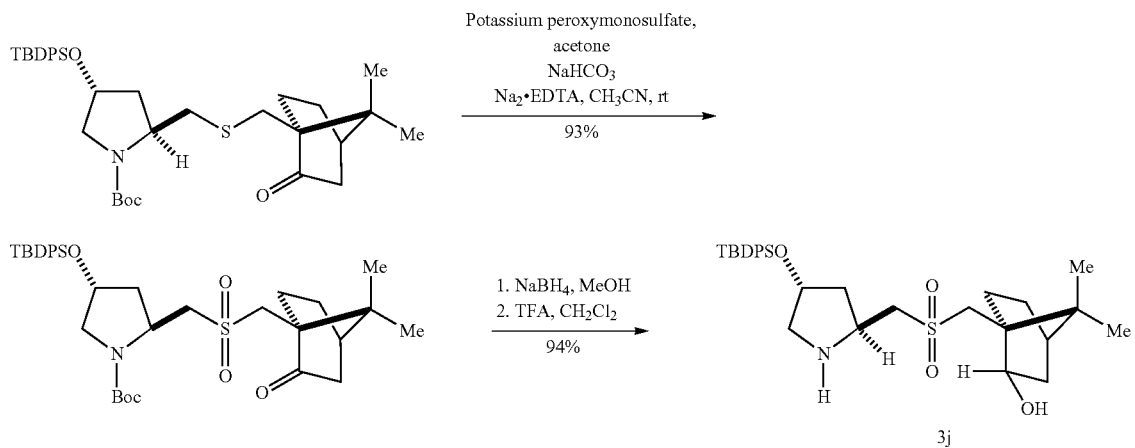

Figure 10A:
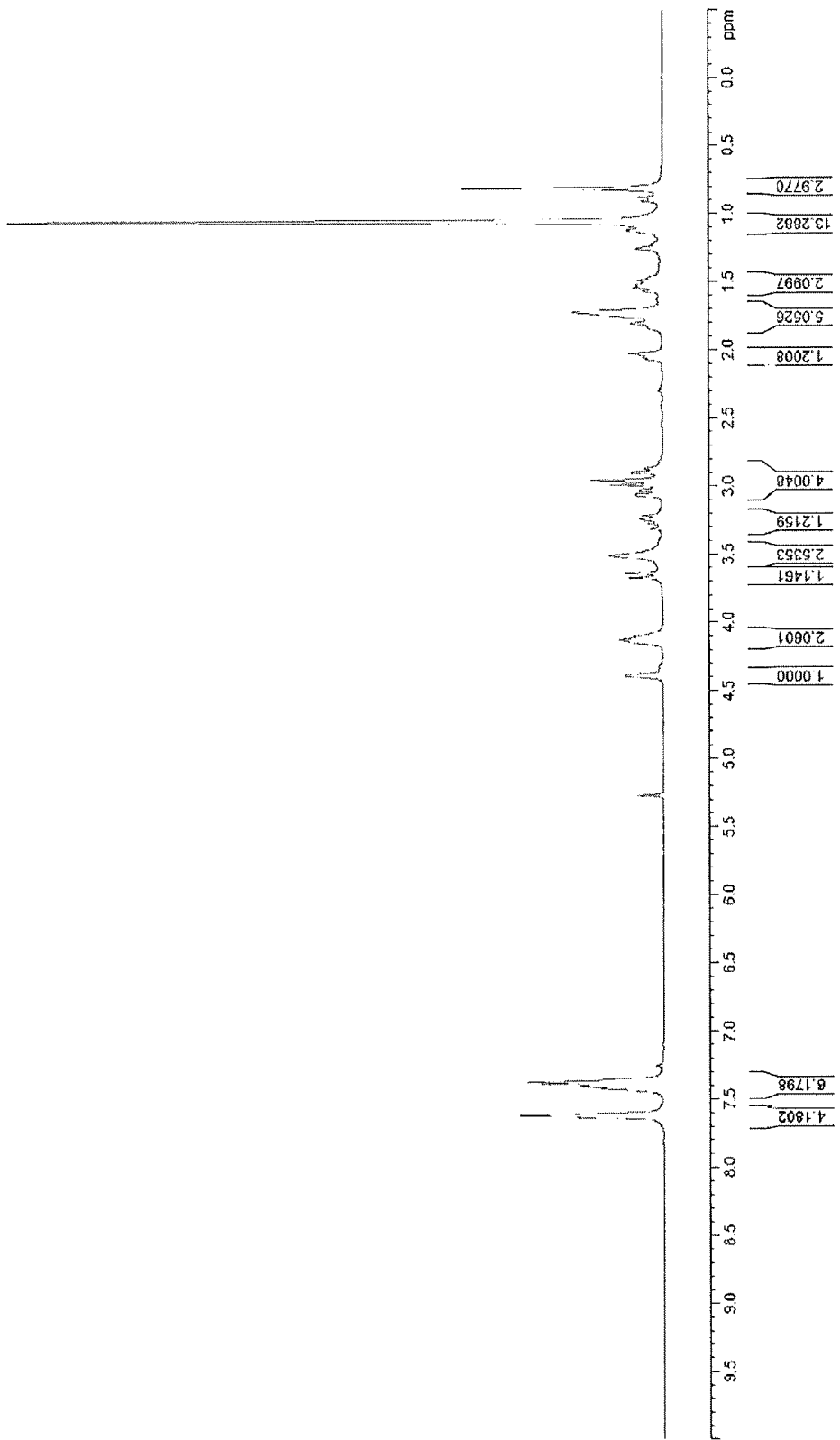
FIG. 10A shows $^1$H NMR of the organocatalyst 3j according to the present invention.
Figure 10B:
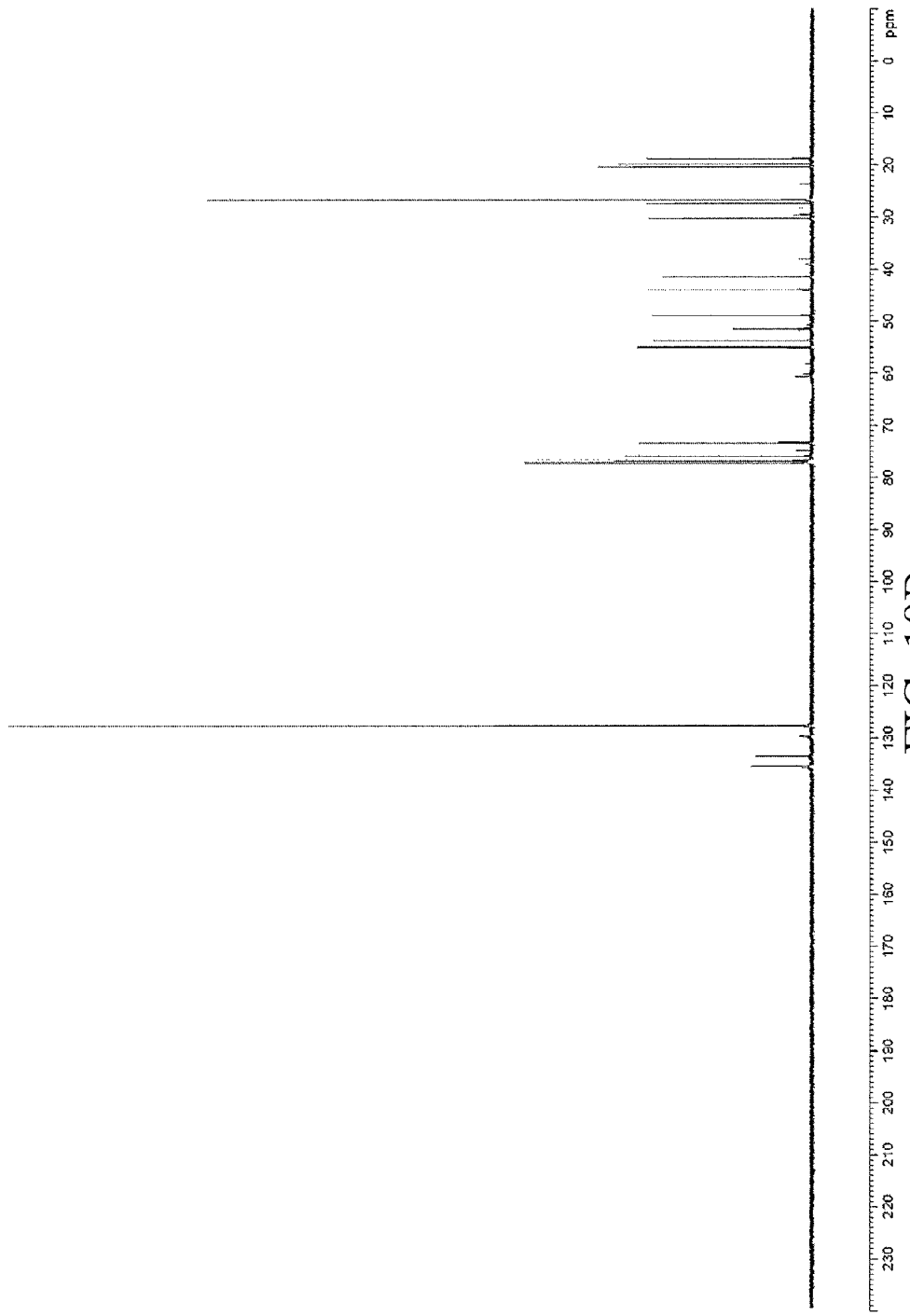
FIG. 10B shows $^{13}$C NMR of the organocatalyst 3j according to the present invention.

At room temperature, the crude product (1.0 g, 1.5 mmol) having sulfonyl group was dissolved in 20 ml of mixed solution of dichloroethane and methanol (volume ratio 1:1), and then NaBH$_4$ (0.3 g, 7.5 mmol) was added into the mixture. The reaction was performed with stirring for 1 hour, and then the reaction was stopped by ammonium chloride solution. The mixture was washed by saline solution, dried by magnesium sulfate, filtered, and concentrated under reduced pressure to obtain a crude product. The crude product was dissolved in 10 ml of dichloroethane, and then 1 ml of trifluoroacetic acid (TFA) was dropped into the mixture at room temperature. The mixture was stirred for 1 hour, and then diluted with dichloroethane. Then, the mixture was washed with sodium carbonate solution. The mixture was then washed by saline solution, dried by magnesium sulfate, filtered, concentrated under reduced pressure, and purified by column chromatography to obtain the organocatalyst 3j. Upon determination, $^1$H NMR and $^{13}$C NMR of the compound 3j were shown in FIG. 10A and FIG. 10B, respectively. $^1$H NMR (400 MHz, CDCl$_3$) δ 7.63 (t, J=6.0 Hz, 4H), 7.43-7.38 (m, 6H), 4.15-4.10 (m, 2H), 3.66 (d, J=13.6 Hz, 1H), 3.51 (s, 2H), 3.31-3.22 (m, 1H), 3.07-2.87 (m, 4H), 2.07-2.03 (m, 1H), 1.84-1.73 (m, 5H), 1.57-1.46 (m, 2H), 1.06 (s, 12H), 0.82 (s, 3H); $^{13}$C NMR (100 MHz, CDCl$_3$) δ 135.5, 133.6, 129.7, 127.6, 75.9, 73.3, 60.6, 55.1, 53.8, 51.6, 50.1, 48.9, 44.0, 41.5, 39.1, 30.3, 27.4, 26.8, 20.4, 19.8, 18.9; IR (CH$_2$Cl$_2$) ν 3491, 3077, 2952, 2856, 1653, 1591, 1473, 1307 cm$^{-1}$; HRMS (EI) C$_{31}$H$_{45}$NO$_4$Ssi calculated as 555.2839; 555.2830; [α]$^{33}_D$–12.1 (c 1.00, CHCl$_3$)

Embodiment 11

Test of Catalytic Activity of the Organocatalyst of the Present Invention in Michael Addition Reaction The organocatalyst 3b was used as an example. Table 1 illustrates the increased yield and enantioselectivity of Michael addition reaction in the presence of the organocatalyst of the present invention.

As shown in Scheme 11, isobutyraldehyde (compound 4a, 0.08 mmol) was mixed with trans-β-nitrostyrene (compound 5a, 0.2 mmol) and the organocatalyst 3b, and the conditions of reaction were shown in Table 1.

Scheme 11

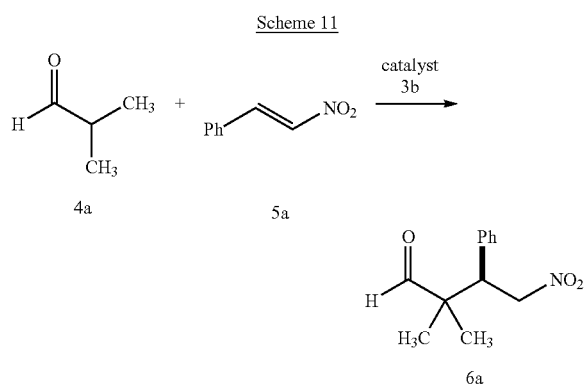

As shown in Table 1, in the reactin with saline solution as solvent, the yield and enantioselectivity (Ee) were further improved by increasing the amount of the catalyst; especially, the reaction time was reduced. While toluene was used as the solvent, the product 6a with higher enantioselectivity was obtained in 3 days. It was found that the solvent with low polarity was more advantageous to the yield and enantioselectivity. The organocatalysts of the present invention had catalytic activity in aqueous solution. Further, it is found that in solvent-free condition of the reaction such as No. 5 reaction, the organocatalyst of the present invention had similar or even better catalytic efficiency, which can facilitate the pharmaceutical production with low environmental pollutions and toxicity-free.

In addition, in one embodiment, it was found that Bronsted acid enhanced the formation of enamine, and further improved the reactivity and organocatalyst. In one embodiment, the acid was p-toluenesulfonic acid, acetic acid, citric acid or benzoic acid, and was preferably benzoic acid, which is 15-25 mol % of the amount of trans-β-nitrostyrene. As shown in the results of No. 8 to No. 10 in Table 1, the excellent yield and enantioselectivity can be obtained at the temperature ranging –5 to 30° C. and shorter reaction time (such as a half day to one day).

Embodiment 12

Test of the Organocatalyst of the Present Invention in Michael Addition Reaction of Donor Molecules and Acceptor Molecules The organocatalyst 3b was used as an example. Table 2 illustrates the increased yield and enantioselectivity of the reactions in the presence of the organocatalyst of the present invention.

As shown in Scheme 12, isobutyraldehyde (compound 4a, 0.08 mmol) or cyclopentanaldehyde was (compound 4b, 0.08 mmol) was mixed with compound 5a to compound 5m (0.2 mmol) listed in Table 2 and Table 3 and the organocatalyst 3b in the presence of 20 mol %, and the reaction was performed at 0° C. for the reaction time listed in Table 2.

TABLE 1

| No. | catalyst (mol %) | solvent | acid | Temp. (° C.) | time (day) | 6a (yield %) | Ee (%) |
|---|---|---|---|---|---|---|---|
| 1 | 10 | saline | — | 0 | 7 | 45 | 68 |
| 2 | 15 | saline | — | 0 | 5 | 56 | 67 |
| 3 | 20 | saline | — | 0 | 5 | 80 | 77 |
| 4 | 20 | toluene | — | 0 | 3 | 42 | 70 |
| 5 | 20 | — | — | 0 | 2 | 62 | 75 |
| 6 | 20 | — | p-toluenesulfonic acid | 30 | 2 | 90 | 71 |
| 7 | 20 | — | acetic acid | 30 | 2 | 67 | 77 |
| 8 | 20 | — | citric acid | 30 | 1 | 77 | 78 |
| 9 | 20 | — | benzoic acid | 30 | 0.5 | 77 | 79 |
| 10 | 20 | — | benzoic acid | 0 | 1 | 88 | 85 |

Ee (%) was determined by chiral HPLC.

Scheme 12

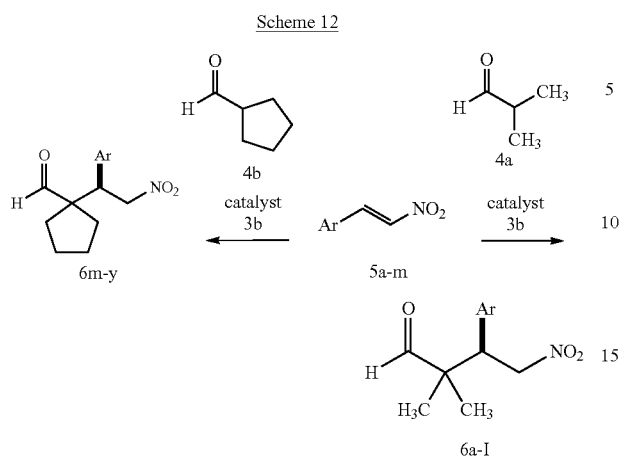

Ar is phenyl (5a), 4-methylphenyl (5b), 2-methoxyphenyl (5c), 3-methoxyphenyl (5d), 4-methoxyphenyl (5e), 2-trifluoromethylphenyl (5f), 3-trifluoromethylphenyl (5g), 2-bromophenyl (5h), 3-bromophenyl (5i), 4-bromophenyl (5j), 3-chlorophenyl (5k), 4-chlorophenyl (5l), or 2-thienyl (5m).

TABLE 2

| No. | 4 | 5 | 6 | Time (day) | Yield (%) | Ee (%) |
|---|---|---|---|---|---|---|
| 1 | 4a | 5a | 6a | 1.0 | 88 | 85 |
| 2 | 4a | 5b | 6b | 0.5 | 89 | 84 |
| 3 | 4a | 5c | 6c | 3.0 | 92 | 71 |
| 4 | 4a | 5d | 6d | 0.5 | 88 | 85 |
| 5 | 4a | 5e | 6e | 0.5 | 96 | 83 |
| 6 | 4a | 5g | 6g | 0.5 | 88 | 85 |
| 7 | 4a | 5i | 6i | 0.5 | 89 | 85 |
| 8 | 4a | 5j | 6j | 0.5 | 98 | 84 |
| 9 | 4a | 5k | 6k | 0.5 | 92 | 85 |
| 10 | 4a | 5l | 6l | 0.5 | 88 | 84 |
| 11 | 4b | 5a | 6m | 1.0 | 95 | 93 |
| 12 | 4b | 5b | 6n | 1.0 | 95 | 93 |
| 13 | 4b | 5c | 6o | 0.5 | 99 | 81 |
| 14 | 4b | 5d | 6p | 0.5 | 99 | 92 |
| 15 | 4b | 5e | 6q | 0.5 | 94 | 88 |
| 16 | 4b | 5f | 6r | 3.0 | 80 | 77 |
| 17 | 4b | 5g | 6s | 1.5 | 90 | 94 |
| 18 | 4b | 5h | 6t | 1.0 | 85 | 80 |
| 19 | 4b | 5i | 6u | 0.5 | 84 | 92 |
| 20 | 4b | 5j | 6v | 1.0 | 86 | 92 |
| 21 | 4b | 5k | 6w | 0.5 | 87 | 92 |
| 22 | 4b | 5l | 6x | 1.0 | 97 | 92 |
| 23 | 4b | 5m | 6y | 1.0 | 95 | 89 |

TABLE 3 compound (Structures 5a through 5m: substituted β-nitrostyrenes with Ar groups as listed above.)

As shown in Table 2, the organocatalyst of the present invention has excellent catalytic activity in the addition reaction of various donor molecules and acceptor molecules, in which the yield and enantioselectivity of the reaction were more than 90%. Upon investigation, it was found that the organocatalyst of the present invention had the group from ketopinic acid, forming the stereo block, and the enamine intermediate was formed from the organocatalyst and the donor molecule, such that when the acceptor molecule interacted with the organocatalyst via the hydrogen bond, the acceptor molecule can only interact with the donor molecule via the position with less block, resulting in the high enantioselectivity.

Embodiment 13

Test of the Catalytic Activity of the Organocatalysts of the Present Invention in Asymmetric α-amination Reaction The organocatalyst 3a and 3b were used as examples. Table 4 illustrates the increased yield and enantioselectivity of the asymmetric α-amination reaction in the presence of the organocatalyst of the present invention.

As shown in Scheme 13, in the presence of the organocatalyst (5 mol %), the azo compound, such as dibenzyl azodicarboxylate (compound 8, 0.5 mmol) was mixed with α-mono-substituted aldehyde 7a-7f (2.0 mmol) and the organocatalyst (0.025 mmol). The reaction was performed at −40° C. for the reaction time listed in Table 4. Then, the reduction was performed with $NaBH_4$ at 0° C. for 5 minutes so as to obtain the product 9a-9f.

Scheme 13

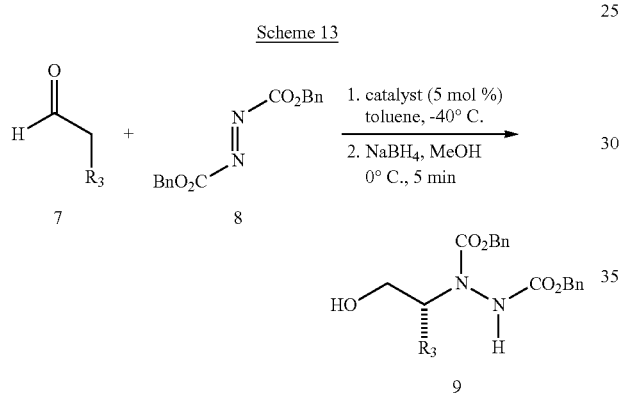

TABLE 4

| No. | $R_3$ | Time (hr) | product | Yield (%) | Ee (%) |
|---|---|---|---|---|---|
| 1 | methyl (7a) | 2 | 9a-(R) | 92 | 97 |
| 2 | ethyl (7b) | 2 | 9b-(R) | 70 | 99 |
| 3 | propyl (7c) | 2 | 9c-(R) | 73 | 99 |
| 4 | propyl (7d) | 2 | 9d-(R) | 64 | 95 |
| 5 | butyl (7e) | 2 | 9e-(R) | 77 | >99 |
| 6 | butyl (7f) | 1 | 9f-(R) | 55 | 95 |
| 7 | methyl (7a) | 2 | 9a-(R) | 60 | 95 |

In the reaction No. 7, the catalyst was the organocatalyst 3a. The catalysts in the remaining reactions were organocatalyst 3b.

As shown in Table 4, in the presence of the organocatalysts of the present invention, the asymmetric α-amination reactions of various α-mono-substituted aldehydes had good or even excellent yield (52-90%) and enantioselectivity (more than 95%). In this embodiment, the amount of the catalyst can be 5-20 mol %, and the reaction was performed at a temperature ranging from −20 to −40° C. The amount of the catalyst was preferably 5 mol %.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. An organocatalyst of formula (I),

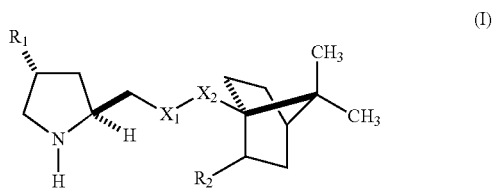

wherein $R_1$ is —H, —OH, —O—Si($R_4$)($R_5$)($R_6$) or $C_{1-6}$alkoxy, in which $R_4$, $R_5$ and $R_6$ are identical or different and independently selected from the group consisting of $C_{1-6}$alkyl; phenyl and phenyl substituted with $C_{1-6}$alkyl; and $X_1$ is different from $X_2$, wherein:
$X_1$ is —S—; $X_2$ is —CH$_2$—; and $R_2$ is —OH or =O, or
$X_1$ is

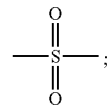

$X_2$ is —CH$_2$—; and $R_2$ is —OH or =O.

2. A method of using the organocatalyst of claim 1 for a Michael addition reaction of a donor molecule and an acceptor molecule, comprising reacting a donor molecule and an acceptor molecule in the presence of the organocatalyst of claim 1, wherein the amount of the organocatalyst is 5 to 25 mol% of the amount of the acceptor molecule, and wherein the reaction is performed in a solvent-free condition, at a temperature ranging from −5 to 30° C., for 12 to 60 hours.

3. The method of claim 2, wherein the addition reaction includes an acid, which is 15 to 25 mol% of the amount of the acceptor molecule.

4. The method of claim 3, wherein the acid is p-toluenesulfonic acid, acetic acid, citric acid or benzoic acid.

5. The method of claim 3, wherein the acid is p-toluenesulfonic acid.

* * * * *